(12) United States Patent
Fontaine et al.

(10) Patent No.: US 8,163,561 B2
(45) Date of Patent: Apr. 24, 2012

(54) METHOD FOR DEPTH RESOLVED SENSING OF BIOLOGICAL ENTITIES BASED ON SURFACE PLASMON RESONANCE SENSORS

(75) Inventors: Norman Henry Fontaine, Painted Post, NY (US); Joydeep Lahiri, Painted Post, NY (US); Guangshan Li, Painted Post, NY (US); Anping Liu, Big Flats, NY (US); Jinlin Peng, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 242 days.

(21) Appl. No.: 12/627,463

(22) Filed: Nov. 30, 2009

(65) Prior Publication Data

US 2011/0171746 A1    Jul. 14, 2011

(51) Int. Cl.
*G01N 21/00*    (2006.01)
(52) U.S. Cl. .................................... 436/164; 356/445
(58) Field of Classification Search .................. None
See application file for complete search history.

(56) References Cited

U.S. PATENT DOCUMENTS

| 6,661,520 B1 * | 12/2003 | Lin et al. ........................ 356/445 |
| 6,956,651 B2 * | 10/2005 | Lackritz et al. ............... 356/445 |
| 2002/0182631 A1 | 12/2002 | Schurmann-Mader et al. .. 435/6 |

FOREIGN PATENT DOCUMENTS

| WO | WO 8706956 A1 | 11/1987 |
| WO | WO 97/09618 | 3/1997 |
| WO | WO01/43875 | 6/2001 |
| WO | WO 0243856 A2 | 6/2002 |
| WO | WO 2007106069 A2 | 9/2007 |
| WO | WO 2007118714 | 10/2007 |

OTHER PUBLICATIONS

Lirtsman et al. "Infrared surface plasmon resonance technique for biological studies", Journal of Applied Physics, 2008, v. 103, 014702-1-014702-5, published on-line Jan. 2008.*
Sexton et al. "Characterisation of gold surface plasmon resonance sensor substrates", Sensors and Actuators A, 2008, v. 141 pp. 471-475, published on-line Oct. 2007.*
Homola et al. "Surface plasmon resonance sensors: review", Sensors and Actuators B, 1999, v. 54, pp. 3-15.*
"Biacore. Sensor Surface Handbook", Jul. 29 2010, http://labs.idi.harvard.edu/springer/uploads/Protocols/BiacoreSensorSurfaceHandbookweb.pdf.*
"Biacore X", 2001, http://web.bf.uni-lj.si/bi/sprcenter/BiacoreX.pdf.*

(Continued)

*Primary Examiner* — Yelena G Gakh
(74) *Attorney, Agent, or Firm* — John L. Haack

(57) ABSTRACT

A surface plasmon resonance sensor system including a high refractive index prism, a sensor chip, a light source having multiple wavelengths over a broad range of wavelengths, optical lenses, a photodetector, a data acquisition unit, and as defined herein. The sensor chip can include, for example, a thin layer of silicon and gold on one face of a transparent substrate and the prism adjacent to the opposite face of the transparent substrate. Such an arrangement provides variable penetration depths up to about 1.5 micrometers with a dynamic range for sensing index of refraction changes in a sample that are several times greater than that of a conventional SPR sensor. The disclosure provides methods for using the surface plasmon resonance sensor system for cell assay or chemical assay related applications.

12 Claims, 11 Drawing Sheets

OTHER PUBLICATIONS

M. Golosovsky, et al., "Midinfrared surface-plasmon resonance: A novel biophysical tool for studying living cells", Journal of Applied Physics, (2009), 105, 102036, pgs. 1-11.

Horvath, et al., "Multidepth screening of living cells using optical waveguides", *Biosensor and Bioeleetronics* 24 (2008) pp. 799-804.

* cited by examiner

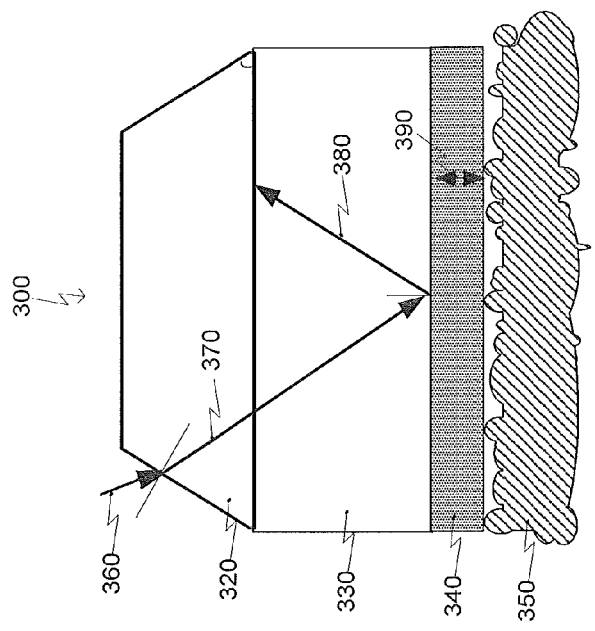
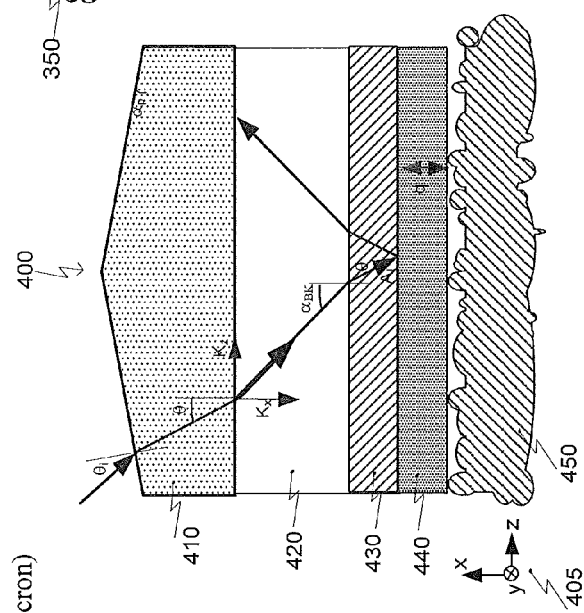
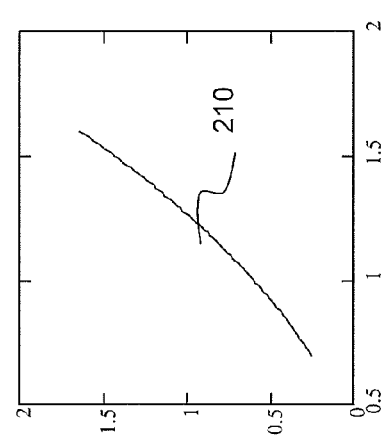
Fig. 2
Fig. 3 [PRIOR ART]
Fig. 4

METHOD FOR DEPTH RESOLVED SENSING OF BIOLOGICAL ENTITIES BASED ON SURFACE PLASMON RESONANCE SENSORS

The entire disclosure of any publication, patent, or patent document mentioned herein is incorporated by reference.

FIELD

The disclosure relates generally to biosensors, biosensor apparatus, and biosensor methods of use.

SUMMARY

The disclosure provides a sensor chip for use in a surface plasmon resonance (SPR) sensor system having variable penetration depth resolution capability. The disclosure also provides a surface plasmon resonance sensor system incorporating the sensor chip. The disclosure also provides methods for using the surface plasmon resonance sensor chip and sensor system for chemical and biological assay related applications.

BRIEF DESCRIPTION OF THE DRAWING(S)

In embodiments of the disclosure:

FIG. 2 shows the relationship of the specimen penetration depth as a function of wavelength for the disclosed SPR sensing system.

FIG. 3 shows for comparison the structure of a prior art SPR chip (300) that consists of a thin metal coating on the glass substrate, and the uncoated surface of the substrate is in contact with the coupling prism.

FIG. 4 shows the general structure of a disclosed silicon-on-glass (SiOG)-based SPR sensor chip.

Figure 11:
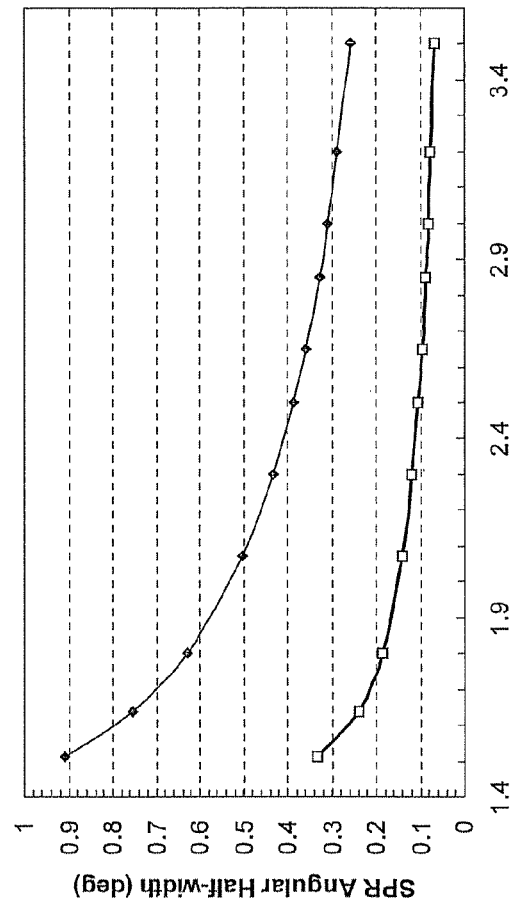

FIG. 11 provides a plot of the angular half-width of SPR responses as a function of refractive index modeled at different wavelengths on various substrates.

Figure 12:
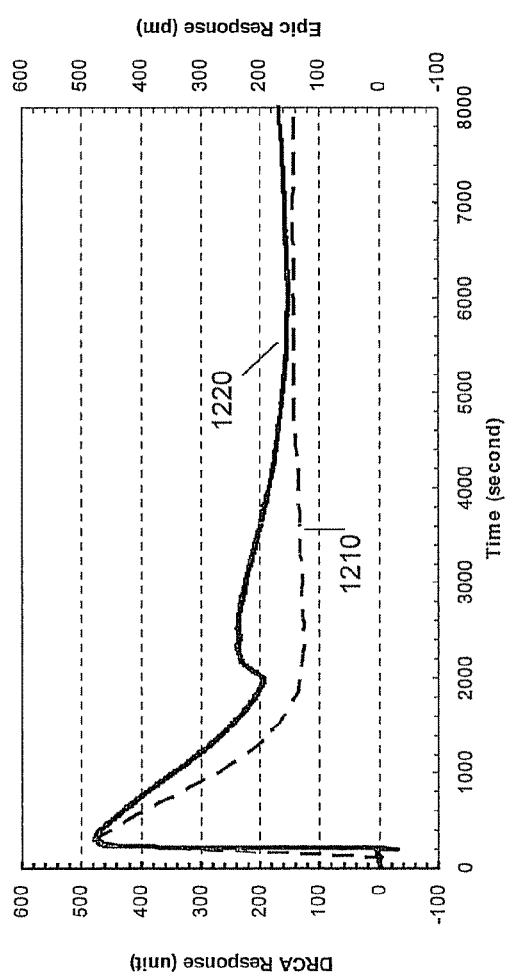

FIG. 12 shows an example of the detection capability for a cell response to adenosine triphosphate (ATP) treatment as measured with a label-independent detection resonance waveguide instrument and the disclosed SPR sensor system.

Figure 13:
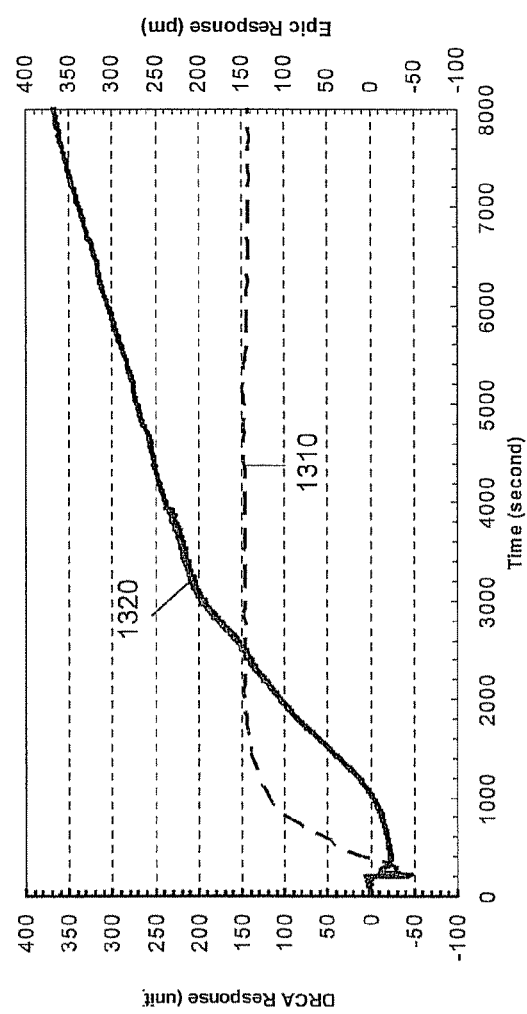

FIG. 13 shows a comparison of cells exposed to epinephrine and as measured by a label-independent detection resonance waveguide instrument and the disclosed SPR sensor system.

Figure 14:
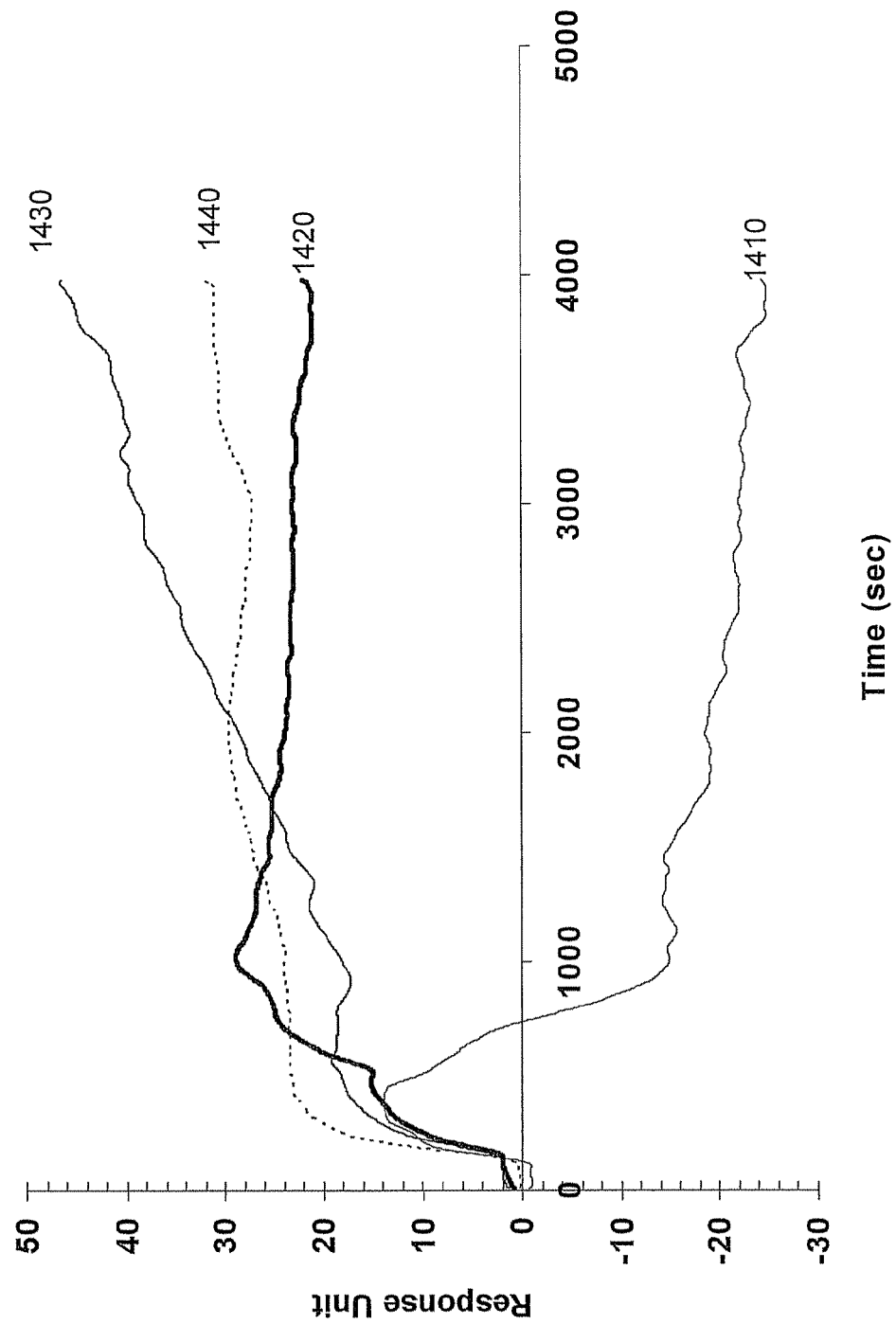

FIG. 14 shows results for bacterial responses to penicillin for Gram-positive (G$^+$) bacteria *B. subtilis* (Bs), and Gram-negative (G$^-$) bacteria *E. coli* (Ec) measured with the disclosed sensor system.

Figure 15:
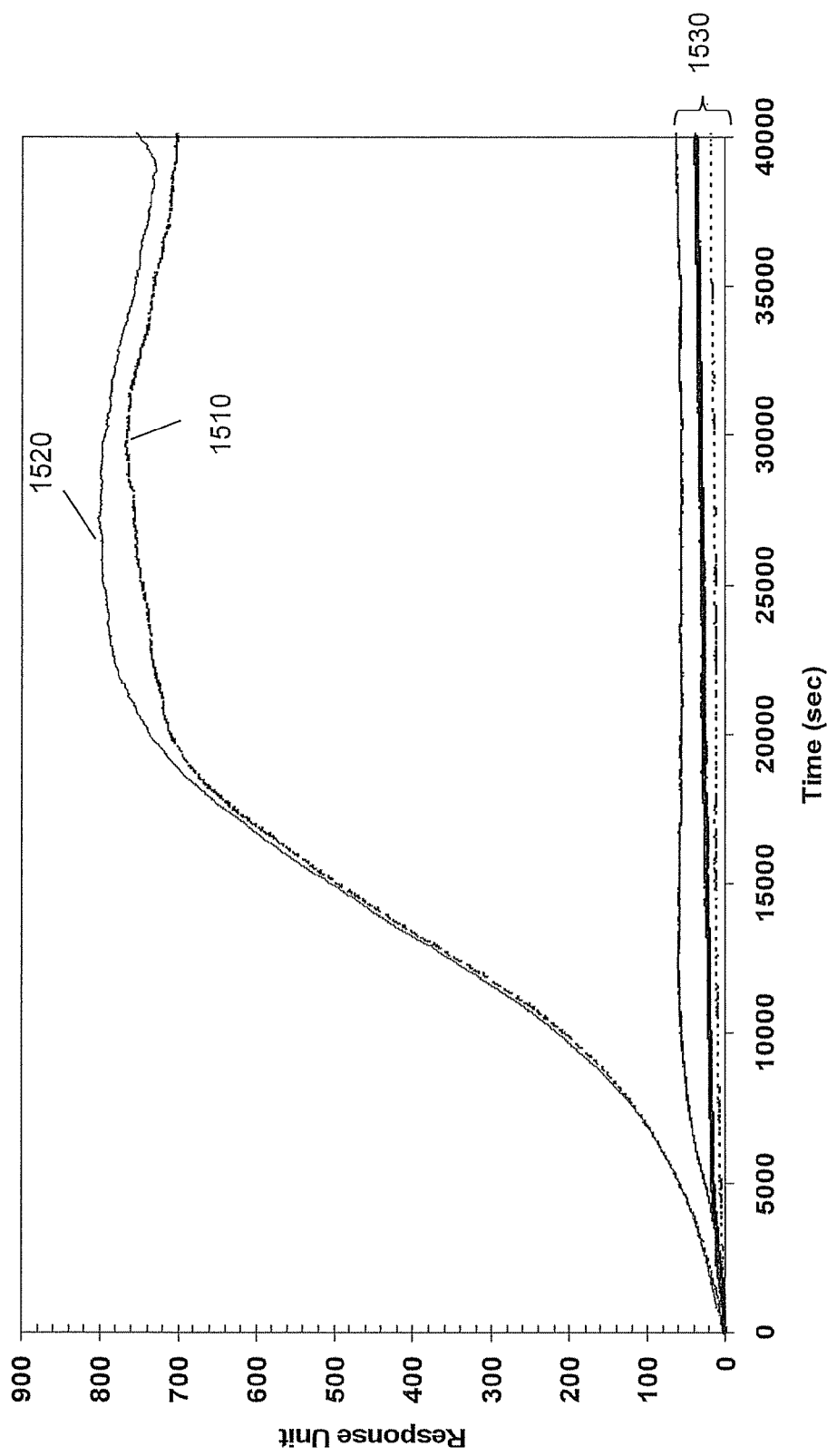

FIG. 15 shows sensor system results for depth resolved bacterial assay responses to ampicillin.

Figure 16:
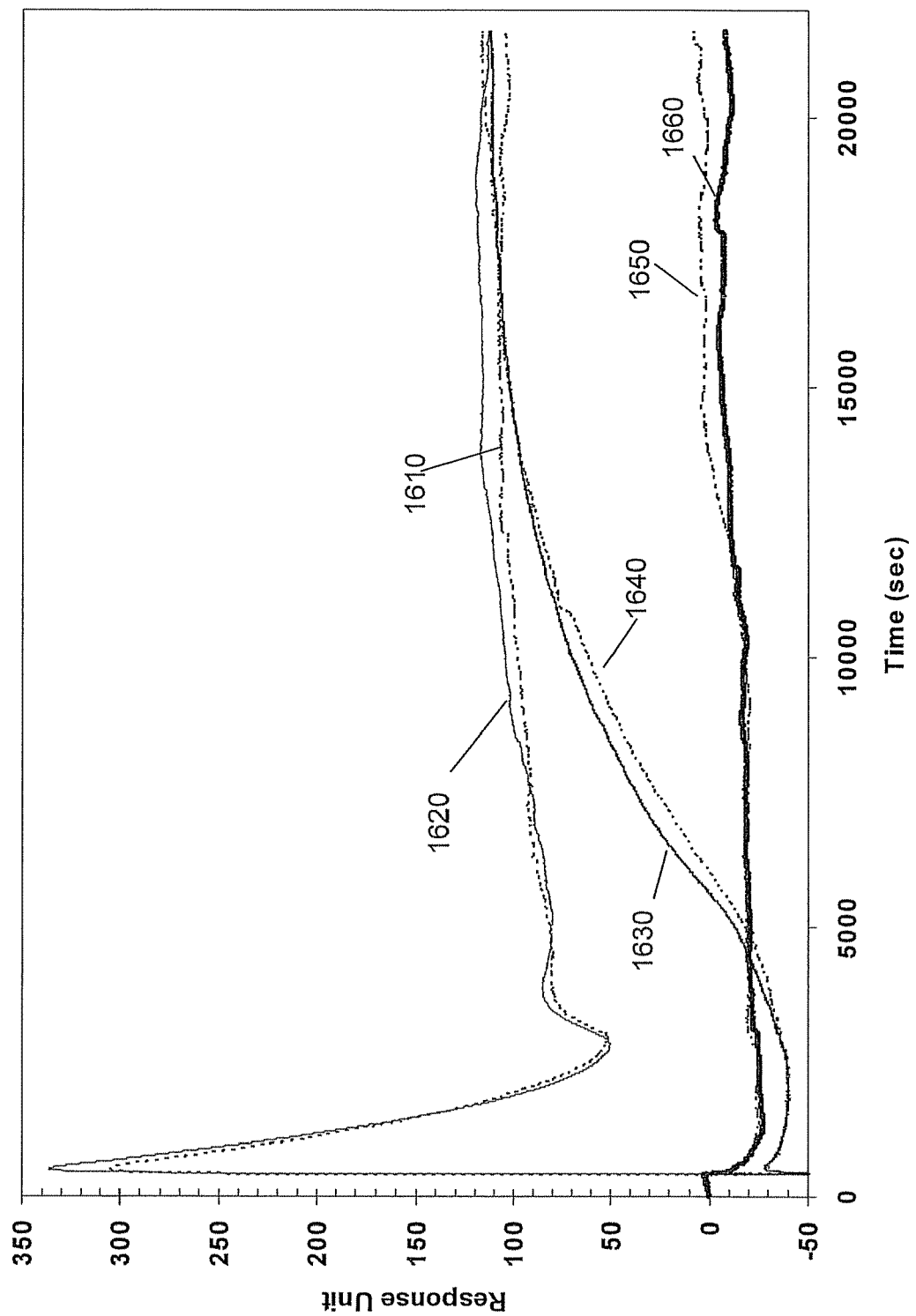

FIG. 16 shows cell assay results for nuclear receptors with modulators measured using depth resolved cellular assay (DRCA) methodology to provide an effective cell-nuclear assay.

Figure 17:
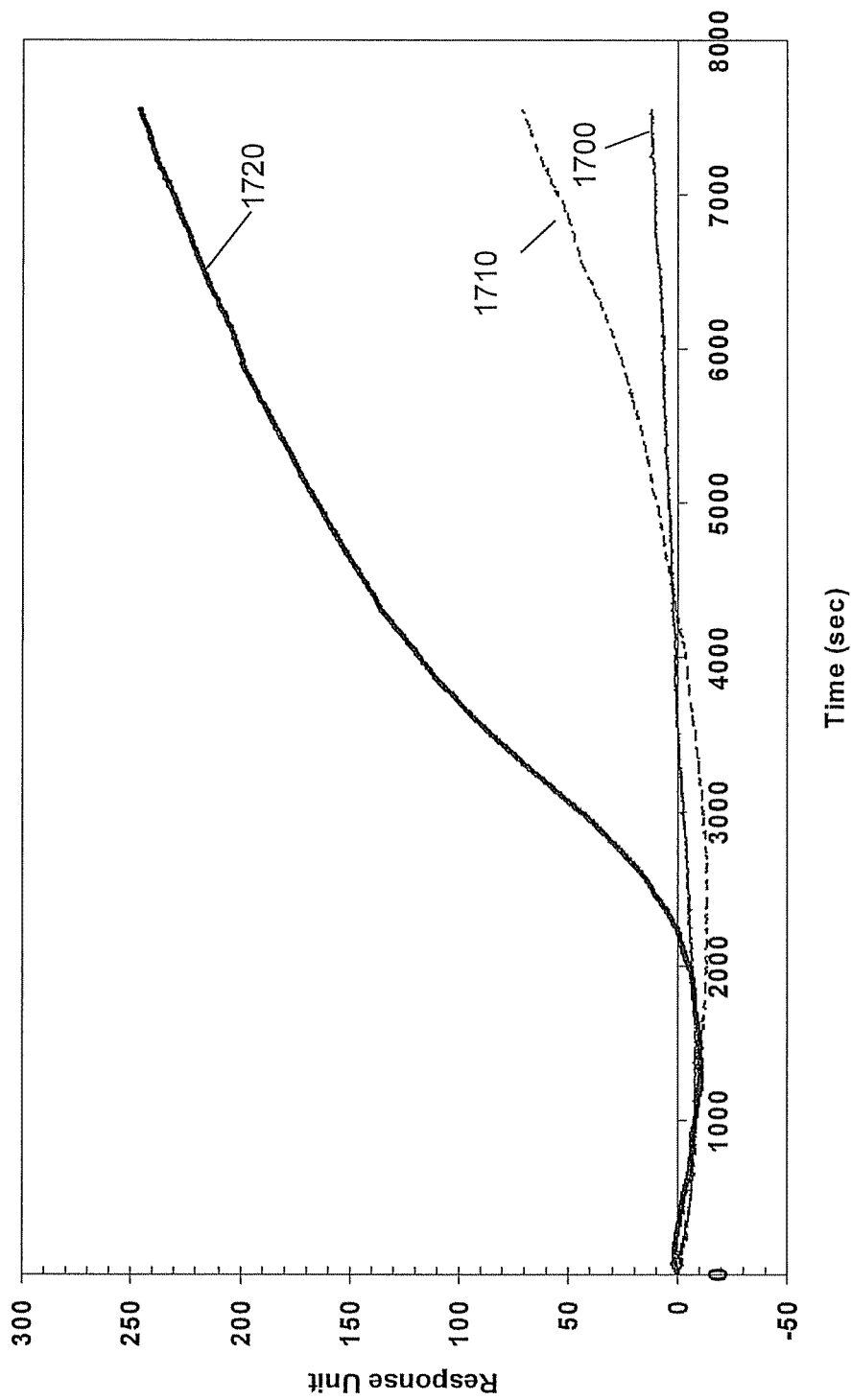

FIG. 17 further demonstrates the specificity of nuclear receptors with DRCA in a cell-nuclear assay.

DETAILED DESCRIPTION

Various embodiments of the disclosure will be described in detail with reference to drawings, if any. Reference to various embodiments does not limit the scope of the invention, which is limited only by the scope of the attached claims. Additionally, any examples set forth in this specification are not limiting and merely set forth some of the many possible embodiments for the claimed invention.

DEFINITIONS

"Effector" or like term refers to a molecule, including the spectrum of small molecules and encompassing any regulatory molecule, including proteins, that can bind to a protein and alter the activity of that protein, or biological cells that interact with other cells.

"Modulator" or like term refers to a molecule that binds to a regulatory site during allosteric modulation and allosterically modulates the shape of the protein, or more generally, any molecule that can trigger another molecular response.

"Include," "includes," or like terms mean encompassing but not limited to, that is, inclusive and not exclusive.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, composites, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto include equivalents of these "about" quantities.

"Consisting essentially of" in embodiments refers, for example, to a variable depth sensor and sensor system, and to a method of making or using the variable depth sensor and sensor system, and articles, devices, or any apparatus of the disclosure, and can include the components or steps listed in the claim, plus other components or steps that do not materially affect the basic and novel properties of the articles, apparatus, or methods of making and use of the disclosure, such as particular additives or ingredients, a particular agent, a particular surface modifier or condition, or like structure, material, or process variable selected. Items that may materially affect the basic properties of the components or steps of the disclosure or that may impart undesirable characteristics to aspects of the disclosure include, for example, unintentional protein denaturation, or like functional disruption or changes to the protein's molecular structure or characteristics by chemical or physical means, which changes could disrupt the cellular or nuclear characteristics of the assay.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, reactants, reagents, polymers, oligomers, monomers, times, temperatures, and like aspects, and ranges thereof, are for illustration only; they do not exclude other defined values or other values within defined ranges. The compositions and methods of the disclosure include those having any value or any combination of the values, specific values, more specific values, and preferred values described herein.

In embodiments of the disclosure, the issue of limited penetration depth of optical biosensor systems and like other evanescent field sensors can be overcome by, for example, the disclosed variable penetration depth SPR sensor system having a light source possessing different wavelengths and having different penetration energetics, as disclosed herein.

In embodiments the disclosure provides a surface plasmon resonance sensor system including, for example, a high refractive index prism, a sensor chip, a light source having multiple wavelengths over a broad range of wavelengths, optical lenses, a photodetector, and a data acquisition unit. The sensor chip can include, for example, a thin layer of silicon and gold on one face of a transparent substrate and a high refractive index prism adjacent to the opposite face of the transparent substrate. Such an arrangement can provide variable penetration depths up to about 1.5 micrometers with a dynamic range for sensing index of refraction changes in a sample that are several times greater than that of a conventional SPR sensor.

In embodiments the disclosure provides a surface plasmon resonance (SPR) sensor system comprising:

at least one light source providing at least one incident beam, the beam having at least two wavelengths;

first optics providing incident beam shaping and beam focusing;

a sensor chip comprising a transparent substrate having on the first face of the substrate a high refractive index prism for receiving the incident focused beam, and having on the second face of the substrate a silicon layer of from about 100 nm to about 5 micrometers, a precious metal layer of from about 30 nm to about 80 nm on the silicon layer;

second optics providing reflected or emitted beam collection;

a photodetector for receiving the collected beam and detecting the SPR signal;

a data acquisition unit.

The system can further include an analyte including, for example, a biological, a biochemical specimen, a cell, a cell component, a cell construct, a surface coating, and like entities, or a combination thereof, on the surface of the metal layer.

The sensor system provides an analyte penetration depth of at least about 0.4 micrometers.

The light source can provide, for example, multiple optical beams having a plurality of different wavelengths over from about 400 to about 1,700 nm. The data acquisition unit can provide, for example, an SPR angular response by finding the angular location of the SPR minimum. The sensor chip has a high refractive index layer having indices from about 2.5 to about 4.0, and the refractive index of the prism is from about 2.5 to about 4.0. The silicon layer on the substrate provides or acts as an optical material having a refractive index of about 3.5. The substrate can be, for example, a glass, a crystal, a semiconductor material, a film coating having a thickness of about 10 to about 100 micrometers, and like entities, or combinations thereof. The substrate can be, for example, transparent, have a refractive index greater than about 2.4, and the substrate can have a low optical loss over the wavelength range of interest. The system can further include, for example, a means for switching the illumination light source, the illumination wavelength, or a combination thereof.

The switching means can comprise a manual human operator switch, an automatic or robotic switch, including an electromechanical device having motive and control features, such as servo motor, microprocessor, micro-switch, or like components, and like switch methods or apparatus, or a combination thereof.

In embodiments the disclosure provides a sensor chip, comprising:

a transparent substrate having a silicon layer of about 100 to about 2,000 nm on the first face of the transparent substrate and a gold layer on the silicon layer; and a high index of refraction prism on the second face of the transparent substrate. The sensor chip can comprise silicon having a thickness of from about 100 to about 1,000 nm.

In embodiments the disclosure provides a surface plasmon resonance method having expanded penetration depths comprising:

providing the above mentioned sensor system, including an analyte, or an equivalent system;

irradiating the analyte with the light source;

detecting an SPR signal with the photodetector;

analyzing the detected SPR signal with the data acquisition unit; and correlating the detected SPR signal with an analyte event. The substrate can be, for example, a material having a high refractive index to mitigate SPR response differences. The SPR signal detection can be accomplished, for example, with a multiple wavelength SPR photodetector, and is free of complex optics. The refractive index of the substrate can be, for example, at least 2.4, and the refractive index of the prism can be, for example, at least 2.4. In embodiments, the light source emits at least two or more wavelengths at from about 0.4 micrometers to about 1.7 micrometers. The expanded penetration depth can be, for example, from about 400 nm to about 1,500 nm. The light source can be, for example, a focused beam to illuminate the analyte and excite SPR.

In embodiments the disclosure provides a method for depth resolved sensing of a biological entity, including for example:

at least one light source providing at least one incident beam, the beam having at least two wavelengths;

first optics providing incident beam shaping and beam focusing;

a sensor chip comprising a transparent substrate having on the first face of the substrate a high refractive index prism for receiving the incident focused beam, and having on the second face of the substrate a silicon layer of from about 100 nm to about 5 micrometers, a precious metal layer of from about 30 nm to about 80 nm on the silicon layer;

second optics providing reflected or emitted beam collection;

a photodetector for receiving the collected beam and detecting the SPR signal;

a data acquisition unit; and a biological entity on the precious metal outer surface layer of the sensor chip surface;

irradiating the sensor with the at least two different wavelengths, each of the different wavelengths providing a different penetration depth;

monitoring each of the different wavelengths for a change in the index of refraction; and correlating the change in the index of refraction to a change in the biological entity.

The above method can further include, for example, contacting the biological entity with a second entity comprising a chemical compound, a biological, or a combination thereof, prior to, during, or after irradiating the sensor with at least one of the two or more different wavelengths.

In embodiments, the biological entity can be, for example, a cell membrane receptor, an intracellular receptor, a cellular nuclear receptor, a subcellular component, and like entities, or a combination thereof. In embodiments, the biological entity can be, for example, a cell, a cell culture, a cell component, a cell construct, a virus, a prion, and like entities, or a combination thereof.

The cell culture can have, for example, a cell density from about 70 to about 100%, the confluence of the cell culture can be, for example, from about 70 to about 100%, and the assay buffer can be, for example, HBSS. In embodiments, the method can further include having the precious metal (such as gold, platinum, chromium, nickel) outer surface layer of the sensor chip having an organic polymer (such as poly-Lysine, poly-ethylene glycol, fibronectin, collagen, laminin, Matrigel, and like materials), or an inorganic (such as calcium phosphate, calcium chloride, and like inorganics or a combination thereof), prior to placing a biological entity on the sensor chip surface.

In embodiments, the biological entity can be, for example, a receptor of a eukaryote cell, a receptor of a prokaryote cell, a synthetic cell construct, or a component thereof, or a combination thereof.

In embodiments, the at least two different wavelengths can be, for example, a plurality of different wavelengths, such as from three (3) to twenty (20) different wavelengths. In embodiments, the second entity can be, for example, a modulator, an effector, or a combination thereof.

Optical sensors based on surface plasmon resonance (SPR) is a most sensitive and accurate technology for label-free detection (e.g., cell, drug, chemical compound) that lie within a few hundred nanometers of the surface. In conventional SPR sensor measurements, a light beam of a selected wavelength is directed through a high refractive index medium to another medium that contains the sample under analysis. In the Kretschmann configuration, a very thin metallic film, (typically of about 40 to about 60 nm of gold) is disposed between the two media. They occur at the interface of a vacuum or material with a positive dielectric constant, and a negative dielectric constant (usually a metal or doped dielectric). When the angle and polarization of the incident beam is properly tuned, it can resonate with an electron gas surface wave mode in the metal film. The resonant coupling conditions are defined by the dispersion relationship of the electron gas, which is itself determined by the metal film and the surrounding dielectric materials. This generates a non-radiating surface electromagnetic wave that is very tightly bound to the metal surface and it propagates in a direction that is within the plane of incidence of the beam and parallel to the plane of the metal film. The energy within the surface plasmon wave is absorbed by the (low) resistivity of the metal film. Light that is incident at the wrong angle or polarization does not couple to the surface plasmon but is instead specularly reflected from the film with very high efficiency. The angle at which the reflected light intensity is at a minimum is due to SPR resonant absorption. The angle at which the reflected intensity is a minimum is very sensitive to index of refraction changes in the material adjacent to the thin gold film. Hence the angle of incidence for SPR absorption can be monitored with a photodetector array. By tracking location change of the minimum intensity of reflected light, biological or biochemical related binding and mass transport events, for example, can be monitored near the surface of the metal film. The technique can be used in many applications, including, for example, cell-based receptor/ligand interactions, noninvasive cell proliferation, and antibody and small molecule affinity analysis. Various SPR sensors, described, for example, in U.S. Pat. Nos. 6,045,756, 5,898,503, 5,912,456, 5,946,083, 6,798,521, and 7407817, have been developed for many manufacturing and analysis applications, including, for example, chemical processing and analysis, process control, and pollution detection. However, these sensors have a fixed penetration depth of about 200 to about 300 nm and are not capable of detecting chemical and biological events at different layers or depths, i.e., having different penetration depths, e.g., above about 300 nm penetration depth.

The SPR resonant absorption is sensitive to changes in mass and binding throughout the volume of the evanescent field that is associated with the SPR resonance. This is of little concern when the binding and mass transport region is known to be confined to a thin layer, e.g., effectively a delta-function of thickness of a few and up to perhaps tens of nanometers, at the surface of the sensor. In that case, the evanescent field of the SPR resonance extends many times the thickness of the binding or mass transport region and the effect of thickness and material perturbations on the probing evanescent field can be ignored to a first approximation. In other designs, a 3-dimensional "scaffold" is used (e.g., Biacore, Matrigel), but the binding and mass transport impart a small effect on the average optical properties of the material in the evanescent field of the SPR resonance. In this instance, the effect of the binding and mass transport on the probing electromagnetic field can also be ignored to a first approximation.

Samples such as cells present a unique problem for SPR detection (and other evanescent field) techniques, because cells are typically much thicker, such as greater than or equal to about 1 micrometer, than the evanescent tail of the typical SPR resonance field of about 250 nm. Hence the entire volume of the evanescent field probes only a fraction of the entire cell depth. This can be problematic because the SPR evanescent field cannot probe some of the interesting structures within the cell, such as the nucleus. Furthermore, intracellular transport processes, such as the transport of material to and from the cell membrane and the cell nucleus, can only be studied in the vicinity of the membrane. In this regard, there may be a number of ambiguities that can occur in the signal because it cannot be directly determined if the change in the SPR signal is caused by the membrane (e.g., invagination and other morphological changes), or mass transport to the membrane though the membrane or away from the membrane either on the interior or the exterior of the cell. Similarly, there is no direct determination of location of binding events throughout the sample volume. Some inferences can be made, depending on prior knowledge of the cell's physiological responses. However, the interpretation of the precise meaning of an SPR response (or of any other evanescent-field sensor's response) signal is not entirely unambiguous. For this reason, it would be highly useful to be able to easily, quickly, and selectively adjust the penetration depth of the evanescent field, so that more than one penetration depth can be sampled simultaneously (i.e., at the same time), sequentially, or both. In this way, one could attempt to compare or contrast signals obtained at different penetration depths to infer that processes are occurring within certain distances from the surface of the sensor. Hence, while it may not be possible to perform a full deconvolution of the depth profile of the mass distribution, binding, and transport changes within the cell samples, the apparatus and method may still allow improved localization and interpretation of SPR responses in cell-based and other dynamic mass redistribution assays.

The penetration depth of a surface plasmon is determined by the wavelength of the light source and the material properties of the sensor and the sampled volumes. For a given sample and sensing system design, the penetration depth cannot vary by much; it is more or less fixed. Since the penetration depth cannot be tuned significantly, no variable penetration depth related information of the dimension of a cell (i.e., greater than or equal to about 1 micrometer) can be collected in conventional SPR measurement systems. For example, in commercially available SPR devices at a commonly used wavelength of 760 nm, the penetration depth is of about 250 to about 300 nm. While this penetration depth can be sufficient for chemical analysis and binding events, it is not suitable for more comprehensive research for cell assay related applications. It is desirable to have a SPR sensor with a larger penetration depth so that evanescent field associated with the surface plasmon resonance can penetrate (and thus probe) most of the cell. This capability enables SPR studies of the interior of the cell, in contrast to the current SPR instrument limitations, which allow only the study of the surface of the cell. In addition, to obtain detailed information about biological events in the cell, it can be desirable to have signals at different penetration depths and to monitor the events from each penetration depth in real time.

The disclosure provides an apparatus, a sensor chip, and method for detecting and monitoring biological and biochemical events that induce refractive index changes of a sample at different depths. This apparatus and method are useful for the purposes of measuring and locating the occurrence of, for example, biological, biochemical, or chemical changes within the sample that lie near the interface of the sensor's metallic (e.g., gold) thin film surface. The disclosed apparatus uses the unique properties of silicon-on-glass (SiOG) chips, which in this instance have been coated with an additional layer of thin (about 40 to about 50 nm) pure gold.

In the angular interrogation method, the SPR response can be detected by measuring the angular location of the minimum from the light reflected by the sensor. The exact angular position can be detected by recording the intensity profile with a photodetector array.

Figure 1:
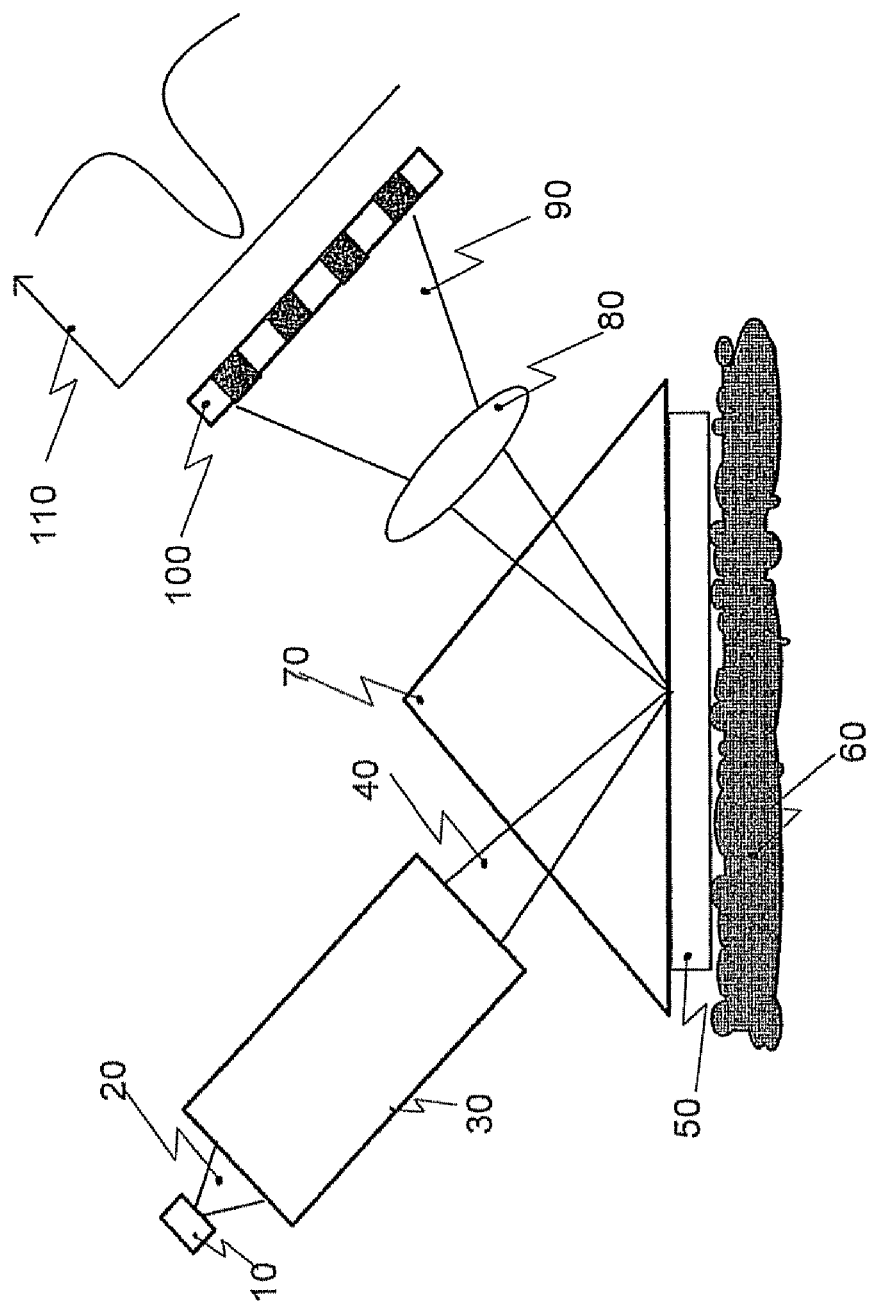
FIG. 1 shows an exemplary schematic of a multi-wavelength SPR sensing system using the sensor chip.

Referring to the Figures, FIG. 1 provides a general schematic of the disclosed SPR sensor system including a measurement apparatus having one or more light sources, several beam shaping optics, a high index of refraction coupling prism, a detection chip, one or more photodetector arrays, and a data acquisition unit. In embodiments, the SPR sensor system can include, for example, a light source (10); having a beam (20) from the light source; beam shaping optics (30); a focused beam (40) for sensing; at least one Silicon-on-Glass (SiOG) chip (50) or like chip(s); a user provided analyte or test specimen (60), such as a cell, a cell component, a cell construct, and like bio-entities; a prism (70); beam shaping optics (80); a reflected or emitted beam (90); a photodetector array (100); and any suitable display, such as a graphical representation of the measured angular response of SPR (110).

A representative system having a single light source and a single photodetector array is illustrated. However, other variations can incorporate, for example, the addition of fiber or free-space couplers, fiber arrays, arrayed optics, beam splitters, or combination thereof, to enable a multiple source, multiple detector measurement, or both features into the apparatus. Although not limited by theory, the incident light excites surface plasmon resonance when the projection of the wave number of the incident light on the surface of the sensor matches that needed to generate the surface plasmon. The excitation of the surface plasmon wave and its subsequent dissipation on the metal film leads to the appearance of a minimum in the intensity versus angular distribution of the reflected light from the metal layer. The angular reflection minimum is extremely sensitive to the dielectric constant in the volume of the sample medium that is probed by the surface plasmon's evanescent field.

The light source of FIG. 1 can comprise, for example, one or more light emitting devices operating at different wavelengths that range from visible to near-IR wavelengths, for example, from about 400 nm to about 1,700 nm. The light sources can also have wavelengths across a large range (e.g., 400 to 1,700 nm). FIG. 2 shows the relationship of the specimen penetration depth for the disclosed sensing system (210). The penetration depth of the evanescent field associated with SPR is a function of wavelength. The longer the wavelength, the deeper the surface plasmon can penetrate. In FIG. 2, it can be seen that the penetration depth can be increased to 1.5 microns when a 1,500 nm light source is used. Compared to a penetration depth of 310 nm from prior art SPR devices, which use a light source that operates at about 760 nm, the penetration depth of the disclosed sensing system is improved by about five fold. FIG. 3 shows the structure of a prior art SPR chip (300) that consists of a thin metal coating (340) on the glass substrate (330). The uncoated surface of the substrate is then contacted with the coupling prism (320). FIG. 4 shows the general structure of a disclosed SiOG based SPR (400) sensor chip. The glass substrate (420) is bonded with a thin layer of, for example, crystalline silicon (430). A metal coating (440) is deposited on the silicon layer for detection. The uncoated face of the substrate is in contact with, for example, a silicon prism (410). An analyte (450), such as a biological specimen, coating composition, chemical compound, or like material or matrix, can be conveniently placed on or near the metal coating (440).

In a conventional SPR, the penetration depth is fixed and detection layer volume is always the same. In contrast, the disclosed system allows for penetration depths that can be as short as 250 nm to more than 1,500 nm. The specific optimal wavelengths for the selected light sources can be selected to lie within the spectral range in which the sample absorption and scattering loss are relatively low. For samples having strong fluorescence emission, the detection wavelength should avoid the fluorescence absorption peak to minimize its impact on index of refraction sensitivity. In contrast, in a system where surface plasmons are to be used to specifically excite, for example, surface fluorescence or quantum dots, the opposite is true, and the wavelength should be selected to lie within the excitation band of the fluor(s) or quantum dots.

In embodiments, the use of multiple wavelengths provides variable detection depths (i.e., penetration depths) so that the sample refractive indices in different depths can be monitored. This information can help analyze biological events or biochemical events. The variable penetration detection depth can be accomplished by measuring SPR responses at a certain first wavelength and then switching the illumination source, preferably rapidly and by automatic means, to a different second wavelength. When the SPR responses at different wavelengths are collected over time, they can be assembled to show the sample's integrated response differences at different penetration depths through that sample. Contrasting the SPR response differences for different wavelengths penults one to monitor the response differences from different depths of the sample.

Many different light sources with a variety of spectral bandwidths can be selected, such as lasers, laser diodes, light emitting diodes (LED), superluminescent diodes (SLD), a white light source, a super-continuum light source, or a combination thereof. The light beams can be delivered to a beam shaper with, for example, free-space optics in which optical mirrors and lenses are used. The light beam can also be delivered, for example, with optical fibers or a fiber bundle. The fiber can be single mode, multimode, or a combination thereof. It can be polarization maintaining fiber when the light sources generate linearly polarized output. The multiple wavelengths can be achieved using, for example, wavelength multiplexing techniques so that all light sources can be combined into one fiber or one beam to simplify optical setup. In this configuration, the measurement is performed at each wavelength. That is, the detector device only takes one data point (SPR response) at any point in time and at any given wavelength. For the following measurement, the wavelength can be changed to a different wavelength for a different penetration depth using optical switching techniques, such as flipping mirrors, galvanometers, and fiber-optic switches. When the light sources are combined by wavelength multiplexing techniques, the wavelength selection can be achieved by, for example, turning on a light source using an optical switch. Although not bound by theory, it is believed that the switching through the span of available wavelengths should preferably be accomplished at a rate that is faster than normal biological or biochemical events are occurring.

The beam shaping optics transform the light output by the source or fiber-optic into desirable beam shapes and provides controlled illumination of the sample area. The beam shaping optics can comprise, for example, a number of optical lenses, a polarizer, and a beam modulation element. The optical lenses shape the beam into a desirable spot size and shape and the proper numerical aperture. The shape of the sensing region can be focused to a point or a line or even as an extended spot. A polarizer can be used to ensure proper light source polarization ("P-polarized", which is parallel to the plane of incidence of the incident beam onto the gold film). For example, to illuminate the sample with a line illumination using a fiber coupled light source, the round beam cross-section needs to be reshaped into a rectangular or an elliptical beam cross-section. This transformation can be accomplished with, for example, a combination of cylindrical lenses and other commonly used lenses, such as spherical, aspherical lenses, diffractive optic beam shapers, mirrors, prisms or a combination thereof. Since only the p-polarization component can couple to the SPR resonance the s-polarization component is not necessary and can potentially impair the ability to detect the SPR minimum of the reflected light. Hence, the polarizer may be needed to block any residual s-polarization component in the incident beam and allow only p-polarized light go through to the test specimen. The beam modulation element is necessary when the spectral width of light source is too narrow (e.g., less than about 0.01 nm) to generate uniform distribution due to commonly known speckles. In this instance, the modulator changes the beam location along p-polarization slightly (e.g., less than about 3 degrees) to minimize speckles and thus improve the signal-to-noise ratio.

In embodiments, the sensor chip can comprise, for example, a glass substrate, a thin (e.g., 10 to 100 nm) layer of silicon, and a thin metal layer atop the silicon layer. In embodiments, the sensor chip can be made by, for example, first, single crystal silicon wafers or tiles are implanted with hydrogen or other ions. Next, a glass substrate is then brought into contact with the implanted surfaces of the silicon. The substrates can be, for example, anodically bonded by applying heat and voltage. Heating the substrates also causes a thin layer of the silicon to exfoliate at the implanted hydrogen layer, resulting in regions of thin, single-crystal layer of silicon attached to the glass substrate. The glass substrate can be any of a variety of glasses which can contain alkaline-earth oxides (e.g., MgO, CaO, SrO, BaO, or combinations) in the glass composition. In embodiments, a thermal expansion match of the glass to the silicon is preferred, which can make LCD display glass, such as Corning Inc., Glass Composition No. 1737 or EAGLE 2000®, excellent choices.

The silicon film thickness can be determined by the ion implantation depth, and can be, for example, from about 200 to about 1,500 nm, and from about 400 to about 500 nm, including intermediate values and ranges. The surface of the silicon layer can be rough, and immediately beneath the outer silicon surface is a region which contains unwanted hydrogen and has a high degree of damage to the crystal structure. Because both of these can adversely affect the performance of devices fabricated from the silicon film, one practice is to polish the surface to remove the damaged layer and reduce the surface roughness. After polishing a furnace anneal can be used to remove any residual hydrogen. For this step either large-area polishing (e.g., chemical mechanical polishing (CMP)) or small-area deterministic polishing (e.g., Zeeko) can be used. Typical film thickness after polishing can be, for example, from about 200 to about 500 nm with good surface quality (rms roughness less than 2 nm).

The metal coating layer can be made of conducting materials such as gold, silver, and like metals, or a combination thereof. The thickness of such a layer can be from about 20 nm to about 80 nm including intermediate values and ranges depending on application and material selection. The metal can be deposited onto the silicon film by, for example, known vacuum techniques, including sputtering and thermal evaporation. In embodiments, a thin gold layer of about 40 nm can be employed because of its excellent chemical resistance. A thin (less than about 5 nm) metal layer can be added between the gold and silicon to improve film adhesion. Chrome or titanium can be particularly useful for this inter-metal layer.

Figure 6:
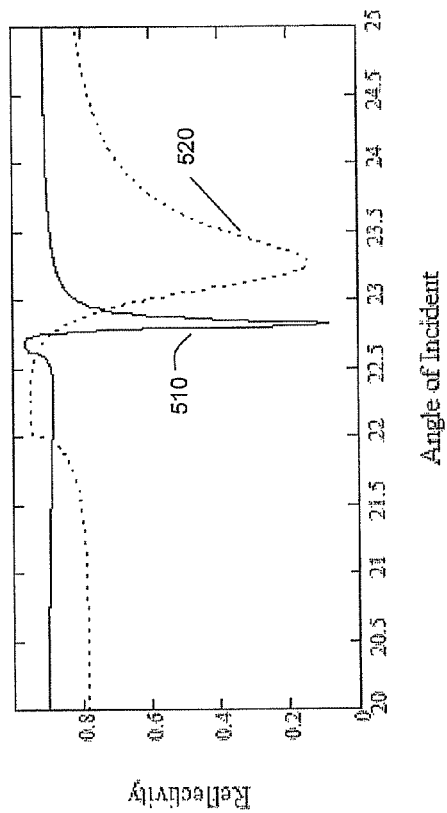
FIG. 6 shows an SPR response with a SiOG chip as the reflectivity as a function of angle of incidence (AoI).
Figure 5:
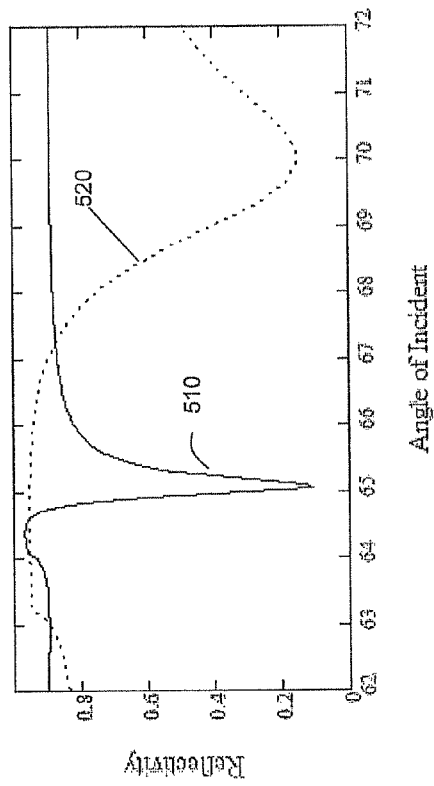
FIG. 5 shows an SPR response with a conventional chip as the reflectivity as a function of the angle of incidence (AoI).

A significant component of the disclosed SPR system is the SiOG sensor chip, which enables a wide dynamic range and multiple penetration depths. A particularly useful property of such chips is that, for example, a two-fold change in light source wavelength from 720 nm to 1,500 nm results in only less than about 0.5 degree of shift in the SPR signal, as shown in FIG. 6. This small angular shift is negligible when the numerical aperture of the incident beam spans several degrees. Since the depth of field (i.e., "depth of focus") along the propagation axis of a low numerical aperture beam is much larger than for a higher numerical aperture beam, the latitude for placing the sample at the focus of a low numerical aperture system is more forgiving than for a higher numerical aperture system. Furthermore, the sensitivity of the wavefront of a low numerical aperture beam can be less sensitive to chromatic and other aberrations as compared to a higher numerical aperture beam. Hence no additional re-alignment is necessary when the light source wavelength is changed, i.e., switched, to accomplish different penetration depths. Thus, all light sources can be launched into the sample surface with the same beam shaping optics. This configuration and capability of the SiOG sensor chip makes variable penetration depths elegantly simple to implement. The small angle of incidence (from 22.75 to 23.25 degrees over 720 to 1,550 nm) also makes the detection unit very compact since it does not need to add additional components to compensate for the angular shift due to wavelength changes. It is impossible to use a similar configuration for a conventional SPR device as shown in FIG. 3 to achieve similar performance. In FIG. 5 the SPR response of a conventional system shifts by approximately 5 degrees when the wavelength is changed from 720 nm (dotted line) to 1,500 nm (solid line). FIG. 6 also shows an SPR response with for disclosed SiOG chip as the reflectivity as a function of angle of incidence (AoI) when the irradiating wavelength is changed from 720 nm (dotted line) to 1,500 nm (solid line).

Therefore, many additional optical, mechanical, or like components may need to be added to the laser source; for example, the beam alignment, the detection unit, or both, to compensate for the large angular shift with wavelength change. Without an active alignment and compensating optical system, due to the ten fold (10×) larger angular shift, a conventional SPR sensing approach would be required to make significant re-alignments for each wavelength to ensure that the detection areas of the sample on the chip would be the same for each wavelength. This re-alignment during the course of a measurement would be time-consuming and slow, and thus very undesirable in a chemical, biological, or biochemical related assay.

The light beam can be coupled into the SiOG chip with a prism having a high refractive index. The prism acts as a light launching element and ensures proper wave number matching to the SPR sensor's plasmon mode. The prism can have a flat surface, or a combination of flat and curved surfaces to reshape the light beam prior to impinging upon the sampling point. To reduce surface reflection, the surface can be coated with an anti-reflection coating. In embodiments, the index preferably can be the same as for silicon. Silicon is one preferred material for constructing the prism when the wavelengths are longer than about 1.2 microns, where it becomes transparent. For a wide range of penetration depths, other materials such as GaP, $TiO_2$, $LiNbO_3$, and like materials, having a high refractive index can be used since they are transparent in both visible (i.e., greater than about 500 nm) and near-IR (i.e., up to 1,700 nm) wavelength. The base angle of the coupling prism can be determined by the refractive index of material. For example, a prism made of GaP can have a base angle of, for example, about 20 to about 25 degrees.

The SiOG chips provide advantages over silicon wafer based sensor chips. With such a thin layer of silicon (less than about 500 nm) on the chip, the optical loss for visible wavelengths is very low compared with a silicon wafer based sensor (i.e., a silicon wafer with a thickness of about 0.5 mm is opaque in visible wavelengths). As a result of the low absorption of the thin silicon layer, the SPR sensor device using the SiOG chip affords the use of a visible light source for highly sensitive refractive index measurement. The use of visible light increases the range of available penetration depths that can be selected, thus allowing the system and sensor to detect refractive index changes in both a very thin layer and a very thick layer of sample near to the sensor's surface. For example, the penetration depth can be reduced to about 77 nm using a light source at about 500 nm.

For high throughput, responses of multiple areas can be detected using a number of photodetector arrays or by optically mapping multiple responses onto a CCD camera by use of, for example, a beam minifying or magnifying system. To improve sensitivity and eliminate environmental variations, an "in-well" referencing scheme can be used, where one sample area on a sensor can be divided into two. One half area is masked with a specific surface chemistry so that the SPR response is insensitive to certain events while the other half area is used to detect biological or biochemical events. The SPR response from the masked area obtains environmental related drifting (for example due to temperature changes) and can be used as a reference. By subtracting the signal from the reference, the correlated noise in the laser, measurement system, and thermal environment can be mitigated. The SPR responses based on angular detection for both conventional and SiOG chips are shown in FIG. 5 and FIG. 6. Compared with a conventional SPR, since SPR minima from the SiOG chip are relatively narrow, one can measure the dip position with higher precision and thus improve the resultant detection sensitivity. Another particularly useful aspect is a wide dynamic range (e.g., about 5 to about 50 times larger than a conventional SPR) which makes it possible to characterize large cellular responses such as those encountered during apoptosis (cell-death) and detachment. This wide dynamic range may extend the uses of the SiOG sensor chip to enable, for example, SPR studies on polymer film growth with relatively high refractive index changes.

Figure 7:
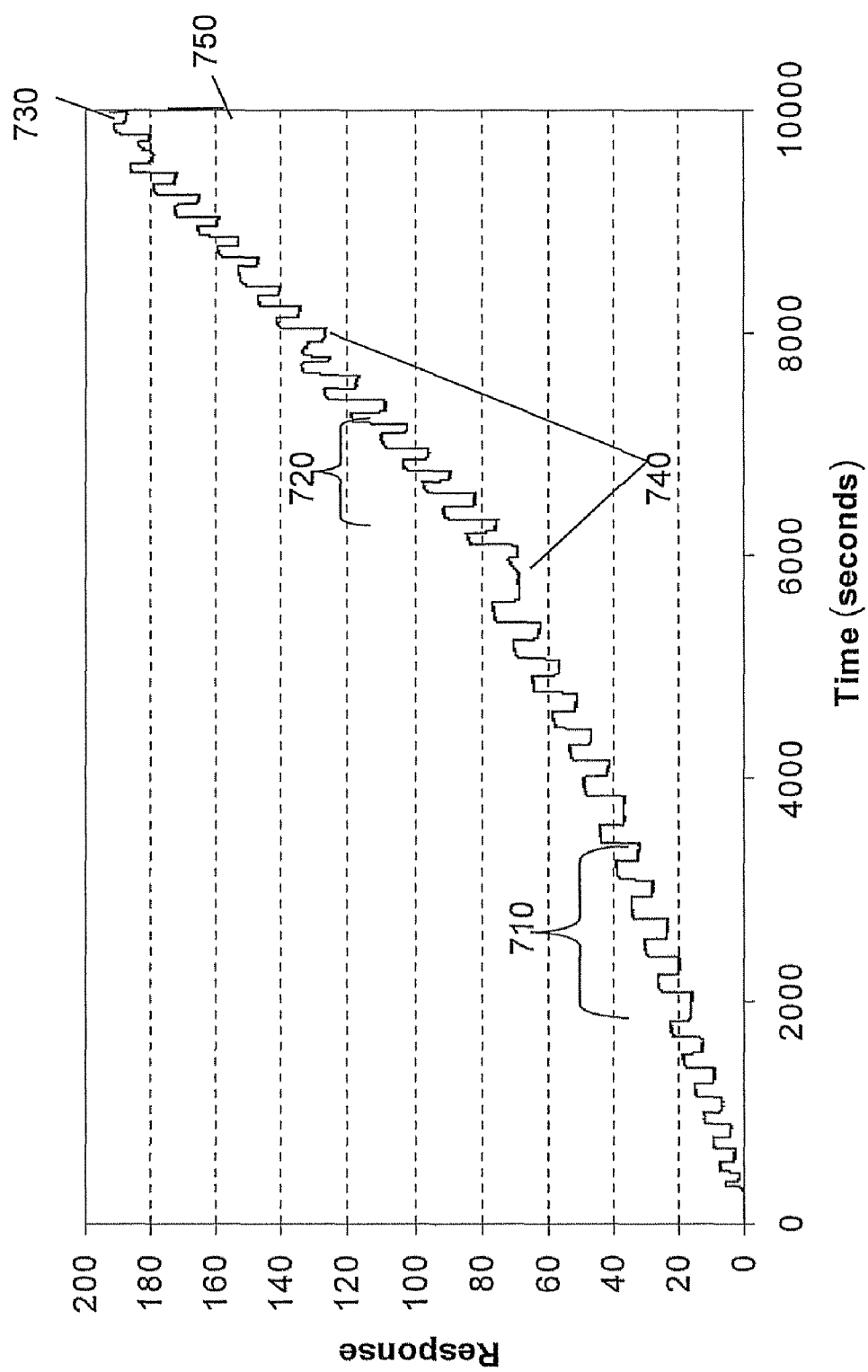
FIG. 7 shows an exemplary measured response of the disclosed SiOG-based SPR system.
Figure 8:
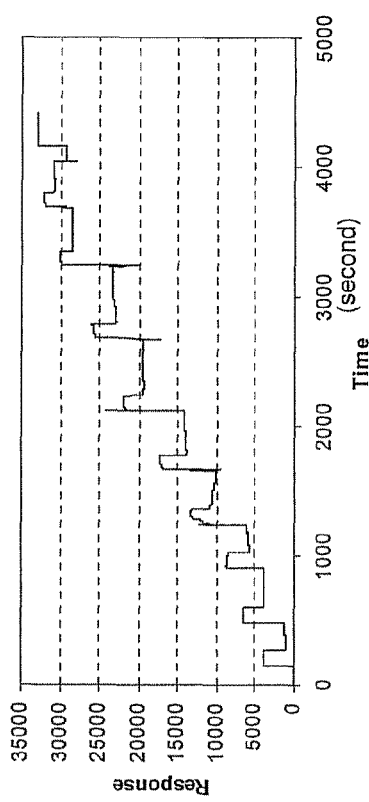
FIG. 8 shows a comparative multilayer response measured with a prior art SPR instrument.

The improved penetration depth of the SiOG sensor chip of the disclosure has been experimentally verified. Comparative experiments were accomplished using the disclosed SiOG-based sensor chip and an SPR measurement system versus a commercially available SPR measurement system and a sensor device. The experimental results are shown in FIG. 7 and FIG. 8. FIG. 7 shows an exemplary measured response with the disclosed SiOG-based SPR system for a layered specimen consisting of alternating polyallylamine hydrochloride (PAH) and polysodium 4-styrenesulfonate (PSS) double-layers. More than eighteen (18) double-layers can be detected; $5^{th}$ double layer (710); $10^{th}$ double layer (720); and $18^{th}$ double layer (730). The apparent non-linear nature of the response curve over time can be an artifact of manually switching the fluidic system; i.e. the period of switching is not constant. The system ran out of angular dynamic range, that is out-of-range (750), but it is evident that the sensor's sensing volume (which is determined by the penetration depth) was not exceeded by the build-up of these layers. The amplitude changes observed after 18 double-layers are nearly the same as the initial double layers, which indicates that the penetration depth of the evanescent field is much greater than the depth of 18 double-layers, which 18 double-layers has an estimated depth or total thickness of about 90 nm. Although the results did not give an exact penetration depth, it is clear that the penetration depths were sufficiently deep for most assay requirements. The distortions at (740) represent pump refill intervals.

The SiOG based system can detect a refractive index change of alternating charged layers of PAH and PSS. Using this SiOG based sensor and the disclosed measurement system, it was possible to detect up to eighteen (18) double-layers, before it reached its dynamic range limitation. Furthermore, since there is little difference in the height steps from the first double-layer to the last ($18^{th}$) double layer, it was possible to also infer that the potential penetration depth of the evanescent field was far from being reached by the growing double-layers.

FIG. 8 shows a comparative multilayer response measured with the prior art SPR instrument (Biacore MUA). The maximum dynamic range for the SPR instrument was limited to five (5) double layers compared to the disclosed SiOG based SPR in FIG. 7. The prior art SPR sensor begins to saturate and become less sensitive to additional layers, as shown by the diminishing amplitude changes (step height) that are observed as the number of added layers increase.

Figure 9:
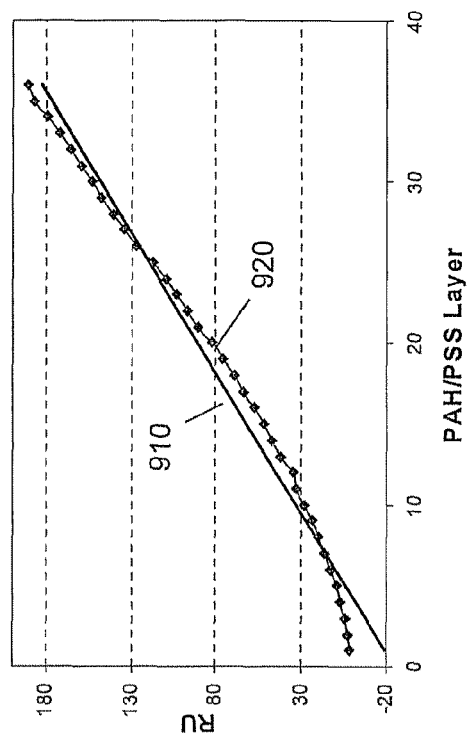
FIG. 9 shows the linearity of the disclosed SiOG-based SPR sensor system response versus PAH/PSS layer thickness.

The commercially available SPR measurement system and sensor chip device could only detect five (5) double-layers and the diminishing amplitudes of the responses that occur as the layer thickness increases is an indication that the addition of layers is saturating that systems ability to measure index of refraction changes farther away from the sensor's surface. The use of the SiOG-based SPR sensor system increased the penetration depth of the SPR's probing electromagnetic field by more than three fold (3×). FIG. 9 shows the linearity of SiOG-based SPR sensor system response (RU; response units in picometers) versus total number of PAH/PSS layers, where $y=5.7918x-25.31$ and $R^2=0.9818$. The linearity of the SPR response based on the SiOG chip over a total of 18 double-layers (910). The linear correlation (910) of the disclosed system is similar to that of the commercially available SPR device (920). Silicon-on-glass (SiOG) concepts are disclosed, for example, in commonly owned and assigned U.S. Pat. Nos. 7,176,528, 7,192,844, and 7,399,681.

Depth Resolved Cell Assay (DRCA)

The disclosed sensor system has been modeled and the modeled details are presented. Experimental results for a cell assay performed with the disclosed SPR sensor system are also presented.

A significant advantage of the disclosed sensor chip, for example, a metalized silicon treated substrate (SiOG) in an SPR sensor system, is the ability to greatly reduce the angular shift of the SPR responses from different wavelengths. Thus, multiple beams with different wavelengths can detect the same sample region without requiring complex optics to compensate for large angular shift, which is a problematic feature in conventional SPR systems using BK7 substrates. The SiOG substrate uses a thin layer of Si as an optical material which provides a refractive index of about 3.5 for detecting light of about 600 nm to about 1,600 nm. The high refractive index of the Si layer on the sensor chip can greatly reduce the angular shift of the SPR responses at the different wavelengths.

Figure 10:
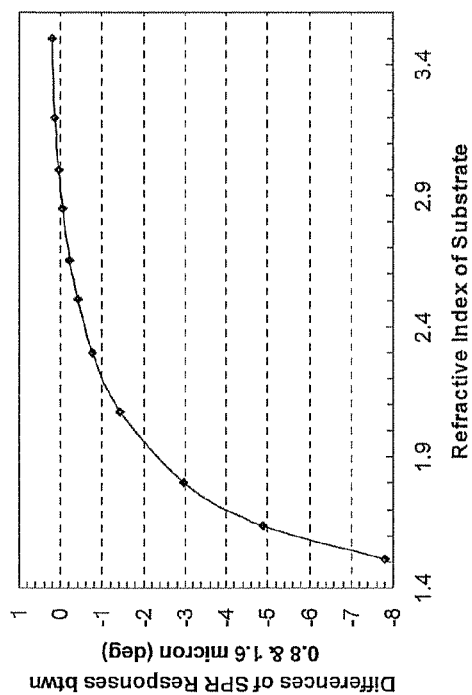
FIG. 10 illustrates the angular differences of SPR responses between the two beams as a function of the substrate's refractive index.

To evaluate how refractive index affects angular shift, SPR responses were modeled at two specific wavelengths: 800 nm; and 1,600 nm (0.8 and 1.6 micrometers). FIG. 10 illustrates the angular differences of SPR responses between the two beams as a function of substrate refractive index. FIG. 10 shows that an increase in refractive index can greatly reduce the angular differences of the two beams. To reduce the angular shift to less than 1 degree, the substrate should have a refractive index greater than about 2.4. More preferably, the refractive index of the substrate can be approximately 3.0 so that the two beams can be completely overlapped. FIG. 11 provides a plot of the angular half-width of SPR responses as a function of refractive index modeled at two wavelengths (upper curve, 0.8 microns; and lower curve, 1.6 microns).

Based on the modeling results it is apparent that SiOG is just one example of many suitable material combinations. Generally, any material with a refractive index greater than about 2.4 can be used as a substrate if the material or material combination is transparent and has a low scattering loss over the wavelength range of interest. The substrate material can be, for example, glass, crystals, semiconductor materials, thin film coatings, and like materials, or combinations thereof.

Another benefit of using high index substrate is to improve system performance. The angular half-width of SPR responses as a function of refractive index were modeled at different wavelengths on various substrates. The results are plotted in FIG. 11. The use of high index materials as the substrate can also reduce the angular width of the SPR response so that its location on the position sensor can be precisely measured. Consequently, a very small angular shift can be readily detected and thus improve device sensitivity.

In embodiments, the disclosed SiOG based SPR sensor and the SPR sensor system can provide variable penetration depth without compromising sensitivity. The use of, for example, a SiOG prepared substrate makes it possible to integrate the device into a very small package. The following lists some details and distinctive features of the disclosed sensor, apparatus, and method compared to conventional SPR systems, and like systems.

Penetration depth increased by greater than five fold (5×). The evanescent field of a conventional SPR has a penetration depth of about 300 nm. The disclosed SPR sensor system can achieve an evanescent field that has up to about a 1,500 nm penetration depth. The use of a long wavelength light source (1,550 nm vs. 760 nm) greatly improves the penetration depth.

Large dynamic range. The use of a SiOG chip produces a very narrow SPR angular response, which enables it to be tracked over a greater range of angular variations. Therefore for a given range of angular input in the incident beam, a large refractive index change (e.g., caused by biological or biochemical events) can be detected.

A wide range of variable penetration depths. The use of a high refractive index prism to couple the light into the sensor surface combined with a multiple wavelength light source make the penetration depth variable without requiring additional alignment for each wavelength change.

High sensitivity. The disclosed SPR chip can be manufactured and finished with a high surface quality and low scattering loss. In addition, the SiOG based SPR sensor generates a narrow SPR signal response, which can be detected more accurately than conventional SPR. This provides a high contrast SPR signal which improves the ability to conduct high sensitivity measurements.

Small size. Unlike conventional SPR, where the incident beam impinges on the metal film at SPR angles of about 60 to about 75 degrees, the disclosed chip and apparatus reduces the SPR angle to less than 25 degrees. As a result, the device is more compact and better-suited for a portable system. The smaller size can also eliminate unnecessary environmental controllers to further reduce system cost.

High versatility. The silicon based sensor chip can be a platform for integrating the SiOG SPR sensor system with other passive and active devices such as laser diodes, nanowires, and photodetectors, which can be produced in high quantities and with good quality using advanced semiconductor fabrication technologies. As a result, a number of more sophisticated and highly sensitive detection technique can be added to the device to achieve multi-function features. Table 1 provides a tabular comparison between conventional SPR and the disclosed SiOG based SPR.

TABLE 1

Comparison between SPR and the disclosed SiOG based SPR.

| Metric/Platform | conventional SPR | SPR with SiOG chip |
|---|---|---|
| SPR angular width (FWHM) @ 1.5 microns | >0.3 deg | <0.1 deg |
| Angular shift vs. wavelength from 720 nm to 1,500 nm | >4 deg | <0.5 deg |
| Angular shift vs. sample index change from 1.30 to 1.42 @ wavelength 1,500 nm | 11.85 | 2.18 |

Depth Resolved Bacterial Assay

In embodiments, the disclosure provides an apparatus and methods for optical sensing with an optical sensor, particularly surface plasmon resonance (SPR) sensors or an angular interrogation system or wavelength interrogation system, for monitoring modulator effects on bacterial cells. Specifically, the disclosure provides conditions for measuring bacterial cell response with the disclosed SPR optical sensor.

Bacteria have a unique cellular structure compared to eurcaryotes, such as having a cell wall. There are two kinds of bacterial cell walls: Gram-positive ($G^+$) and Gram-negative ($G^-$). $G^+$ and $G^-$ bacteria respond differently to a given compound, e.g., an antibiotic. An antibiotic is a natural or synthetic substance that can selectively inhibit the growth of bacteria, or like life form. Antibiotic resistance can be a major public health issue and can impose an enormous financial burden on both the healthcare system and on society generally, because of direct costs due to prolonged illness and treatment in hospital, indirect costs due to loss of productivity, and societal costs due to morbidity and mortality. Antibiotic resistance is an evolutionary process that is based on selection of organisms that have enhanced ability to survive doses of antibiotics that would otherwise be lethal. Antibiotics themselves act as a selection pressure which allows the growth of resistant bacteria within a population and inhibits susceptible bacteria. The underlying molecular mechanisms leading to antibiotic resistance can vary. Intrinsic resistance may naturally occur as a result of the bacteria's genetic makeup. Antibiotic resistance can also spread between different bacteria by plasmid transfer, which may result in co-resistance to multiple antibiotics. The disclosure provides methods for measuring with label-free optical sensors antibiotic effects on bacterial cells.

The thickness of a bacterial cell can be, for example, from about 500 nm to about 10 micrometers. Therefore, at a given depth of a cell, only a specific cellular event may be detected.

To obtain a more comprehensive depiction of biological and chemical activity within a bacterial cell, monitoring and measuring refractive index changes at various depths can provide valuable information, see Example 5 below. However, it can be very challenging to simultaneously monitor different depths with a conventional label-free optical sensor.

Depth Resolved Nuclear Assay

In embodiments, the disclosure provides methods for measuring a nuclear event or nuclear events of a whole cell using the disclosed SPR optical sensor at certain penetration depths.

In embodiments, the disclosure provides methods for using a multiple penetration depth SPR system to monitor and characterize the cell-nuclear response to an effector, such as a modulator compound with depth resolved cell assays.

A nucleus is the control center of a living cell, where for example, DNA replication, and RNA transcription are accomplished. Nuclear Receptors (NRs) play a vital role in regulation of nuclear function. An understanding the complex and ever-growing network of interactions between co-regulatory proteins and nuclear receptors can have major implications for human cell biology but also for the development of new drug treatments of many diseases. Most current studies involve cell destruction and multiple fluorescent labeling. The nucleus is typically away from the plasma membrane of the cell and needs deep optical penetration depth to monitor it.

The nuclear receptor superfamily contains a wide variety of transcription factors, which includes nuclear receptor (NR) and orphan nuclear receptors. Unlike hormones for cell surface receptors, lipophilic hormones can pass through the cell membrane to the cell interiors where nuclear receptors transduce signals from glucocorticoids, mineralocorticoids, the sex steroids (estrogen, progesterone, and androgen), vitamin $D_3$, or thyroid hormones.

The height of a mammalian cell is typically about 1 to about 3 microns. The cell is a structural and functional unit of an organism. Within a cell, there are cytoplasm containing proteins and metabolites, and many organelles such as nucleus, mitochondria, Golgi, and endoplasmic reticulum, all of which play vital roles in cellular function. Therefore, at a given depth of a cell, only a specific cellular event may be detected. To get the more complete picture of what is going on inside a cell, monitoring activities in the organelles located at various depths can provide valuable information. However, it is very challenging to monitor organelle events, such as a nuclear event, using a conventional label-free optical sensor. With conventional SPR optical systems, a large Angle of Incidence change occurs in the SPR signal as the wavelength of the incident beam is varied. Over from about 760 nm to about 1,550 nm, the SPR angle will vary by approximately 4 degrees. Thus, any static optical system for SPR measurement would have to be designed to work across a large numerical aperture (i.e., angular dynamic range). In this case, the range would need to be even greater than 4 degrees. An actively positioned system could be developed, but then it would have to accurately change the incident angle and optically re-align each and every time the interrogation wavelength changed. It is known that active positioning systems can be very undesirable because of their slow operating speeds, they can disturb the assay conditions, they can diminish the multi-wavelength data acquisition speeds, and they can create noise and reproducibility errors. With the disclosed silicon-on-glass SPR biosensor system when the wavelength of the illuminating radiation is doubled from about 760 nm to about 1,550 nm, it will result in only about a 0.4 degree shift of the SPR angle, which is about one-tenth ($1/10^{th}$) of the conventional angle shift. Yet the disclosed silicon-on-glass SPR biosensor system will create a nearly 5-fold increase in the penetration depth, ranging from about 330 nm to about 1,500 nm. In embodiments, the SiOG based SPR sensor can be designed as a static system, while still enabling near-simultaneous multiple wavelength detection over a large range of penetration depths. The SiOG based SPR sensor can do so without a bulky optical layout (with a large numerical aperture) or without a positioning system.

In embodiments, the disclosure provides a method and optical sensor instrument setup to simultaneously assess nuclear events at different depths using, for example, pathway modulators and human cell lines. The following lists some details and distinctive features of the disclosed nuclear assay method and apparatus compared to conventional SPR systems and like systems.

Label-free detection. An integrated signal arising from a nuclear-specific cell response at different depths can be detected and measured by optical sensors. The measured signal includes changes in the refraction index, wavelength, interrogation angle, or combinations thereof.

Real-time living cell assay. The effect of pathway modulators on live cells can be detected as early as less than about 30 seconds after contact. Additionally, the continuous effect/time course of the cell response can be monitored in a single experiment with multiple wavelengths.

Physiologically relevant assay conditions. The disclosed method and apparatus can also accomplish assays with live whole cells in a cell culture medium.

Simple assay process. After cells are grown at the bottom of a treated gold sensor chamber, effector, modulator, or both, are added. One can then measure the kinetic interaction or the end-point readouts using optical sensors such as the DRCA instrument. The disclosed method can be readily automated if desired.

EXAMPLES

The following examples serve to more fully describe the manner of using the above-described disclosure, as well as to set forth the best modes contemplated for carrying out various aspects of the disclosure. It is understood that these examples do not limit the scope of this disclosure, but rather are presented for illustrative purposes. The working examples further describe how to make and use the articles and methods of the disclosure.

Example 1

Method of Making the Sensor Chip and SPR Sensor System

The sensor chip was made from a silicon-on-glass (SiOG) substrate. First, the SiOG chip was made using processes disclosed in U.S. Pat. Nos. 7,176,528, 7,192,844, and 7,399,681. The surface was then polished to provide an optical surface. This substrate was then coated with a layer of gold using conventional metal coating techniques, such as thermal deposition, sputtering deposition, and electron beam deposition. The thickness of the gold layer can be, for example, about 40 nm. To improve adhesion, a thin layer of Ti of thickness of about 5 nm was coated before depositing the gold coating. The sensor chip was then bonded to the bottom of a honeycomb structure to form a microplate. The gold layer can face upwards and can make direct or indirect contact with a biological or biochemical sample.

Example 2

Method of SPR Sensing with the SPR Sensor System The sensor system consists of light sources, a beam shaper, a prism, a CCD camera, and a data acquisition unit. The light sources used in the setup consist of four laser diodes emitting at 650 nm, 800 nm, 980 nm, and 1500 nm. The light beams from these light sources are delivered with single-mode fibers. The beams pass a beam shaper and target the sensor chip through the GaP prism. The sensor chip physically contacts the prism through an index matching oil which has the same refractive index as the glass substrate. The reflected beam can then be collected by the CCD camera and analyzed by the data acquisition unit. During the measurement, each light beam is sequentially turned on and off while the CCD camera records a corresponding picture. The CCD camera only takes a picture of a light source one at a time. The acquired pictures are analyzed by data acquisition unit.

Example 3

DEPTH RESOLVED CELL ASSAY (DRCA). Cell assays were performed using the disclosed SPR sensor system and excellent results were achieved. The disclosed SPR sensor system has from about three (3) to about four (4) times larger specimen penetration depth compared to a Corning® Epic® label-free detection system or a conventional SPR system. The disclosed SPR sensor system is capable of detecting significantly more biological events. Actual and comparative results are shown in each of FIG. 12 and FIG. 13. FIG. 12 shows an example of detection capability for a cell response to ATP (adenosine triphosphate) treated as measured with the label-independent detection resonance waveguide Epic® instrument (1210) and the disclosed SPR sensor system DRCA (1220). Both assays showed a similar response trends over time. However, the disclosed SPR sensor system exhibited more detail for strong responses. FIG. 13 shows an example of cells exposed to epinephrine and measured by the Epic® system (1310) and the disclosed SPR sensor system (1320). The disclosed SPR sensor system can detect biological events as short as, for example, 0.1 second interval since it is a continuous process, whereas the Epic® system detects events in a very longer time interval of about 10 seconds. This result further demonstrates how significant the long penetration depth can be and how multiple penetration depth capability for cell assay can be particularly useful.

Example 4

Depth Resolved Bacterial Assay. To demonstrate the utility of the disclosed SPR sensor system for bacterial cell assays, a cell assay platform using modulators, such as penicillin, has been developed. Penicillins are beta-lactam antibiotics and can be used in the treatment of infections caused by Gram-positive bacteria. Beta-lactam antibiotics inhibit the formation of peptidoglycan cross-links in the bacterial cell wall and can causes cytolysis or death of Gram-positive bacteria having weakened or defective cell wall under the influence of osmotic pressure. In addition, the build-up of peptidoglycan precursors can trigger the activation of bacterial cell wall hydrolases and autolysins, which further digest the bacteria's existing peptidoglycan. The ability to detect a modulator effect on bacterial cells has been demonstrated by measuring the bacterial response(s) triggered by a known modulator using the disclosed SPR sensor system. The disclosed depth resolved cell assay system can be a useful tool for bacterial assays.

As an example, optical sensors including a disclosed SiOG based surface plasmon resonance (SPR) sensor can be used to monitor the effect of an antibiotic on bacteria. Bacterial cells can be cultured and deposited as a thin layer on the sensor's treated gold surface. The cultured bacterial cells can then be treated with a modulator. The bacterial response can be simultaneously monitored using the disclosed multiple wavelength SPR platform, such as the disclosed Corning® Depth Resolved Cell Assay (DRCA) instrument.

The same or a similar setup and assay protocol can be applied to other types of bacterium utilizing variable penetration depths. For example, for some suspension bacterium, a longer wavelength light source, which induces a larger penetration depth, can be used to detect reactions of suspension bacterium without requiring a special surface chemistry on the sensor. Normally, it can be difficult or even impossible to detect reactions of suspension bacterium. In addition, the multiple- or variable-depth capability of the disclosed sensor system can also be adapted to investigate attachment or detachment of bacterium to surface chemistries determined by surface interactions. In this instance, a number of penetration depths can be implemented and their responses simultaneously monitored. With this approach, when and how the bacterium are attached and detached from a surface can be detected.

Detection of Bacterial Response
Bacterial Cell Wall Structure

Gram-positive organisms have a high peptidoglycan cell wall content and the cell walls typically lack the outer membrane found in Gram-negative bacteria. Gram-negative bacteria have a thin peptidoglycan layer and an outer membrane containing lipopolysaccharide. The pathogenic capability of Gram-negative bacteria is usually associated with the outer membrane.

Pathway Modulator

Pathway modulators can have a significant impact on cell biology and can be useful for drug discovery.

FIG. 14 shows results measured with the disclosed sensor system that indicate penicillin had an significant effect on Gram-positive (G$^+$) bacteria *B. subtilis* (Bs) (1410) and had no insignificant effect on Gram-negative (G$^-$) bacteria *E. coli* (Ec) (1420) and *E. coli* with the recombinant pUC19 plasmid (1430). A buffer control measurement is shown as trace (1440).

Ampicillin is a β-lactam antibiotic with an amino group side chain attached to the penicillin structure. Ampicillin is able to penetrate Gram-positive and some Gram-negative bacteria. It differs from penicillin only by the presence of an amino group. That amino group helps the drug penetrate the outer membrane of gram-negative bacteria. Ampicillin inhibits bacterial cell-wall synthesis (peptidoglycan cross-linking) by inactivating transpeptidases on the inner surface of the bacterial cell membrane. Amplicillin can inhibit both *Bacillus subtilis* and *E. coli*, but not *E. coli* with the recombinant pUC19 plasmid. A very small amount of cells, e.g., 0.05 OD from *Bacillus subtilis*, *E. coli*, and *E. coli* pUC were separately inoculated into growth medium plus ampicillin (Ap), e.g., 100 microg/mL. Cell growth was continuously monitored with DRCA. FIG. 15 shows sensor system results for bacterial response to Ampicillin, specifically only *E. coli* with pUC19 (1510) and (1520) survived and grows in the medium with Ampicillin (increasing top two curves). Bs, Ec, and buffer controls are represented by baseline curves (1530). *E. coli* with pUC19 showed a typical bacterial growth curve. The data suggested that DRCA can detect cell growth, mass increase, or both, for bacteria in suspension when on or coming to the sensor surface.

The disclosed bacterial assay is one of many examples of how DRCA can be used for bacteria assays. A similar setup and assay protocol can also be applied to other types of bacterium by using variable penetration depths. This can be especially beneficial for assaying certain bacterial strains which barely attach to the detection surface. In such a situation, a long wavelength light source, which induces a large penetration depth, can be used to detect the reaction of suspension bacteria without requiring a special surface chemistry. The multiple depth capability of DRCA can also be adapted to investigate attachment or detachment of bacterium to various surface chemistries due to biological reactions. In this situation, a number of penetration depths are selected and the responses are simultaneously monitored. The penetration depth of DRCA can be, for example, from about 50 nm to about 2,600 nm, and from about 100 mm to about 1,600 nm, including intermediate values and ranges. With this approach, when and how the bacterium are attached and detached to the surface can be detected. The example demonstrates a simultaneous detection of compound effects on bacterial cells with the DRCA system. The disclosed bacterial cell assay method can used in a variety of applications, including for example, in microbiology, epidemiology, and drug development, and like applications.

Regents, Medium and Bacteria Ampicillin, and penicillin were purchased from Sigma (St. Louis, Mo.). Luria-Bertani (LB) medium and Nutrient broth (NB) were from Invitrogen (Carlsbad, Calif.). *Bacillus subtilis* and *E. coli* were from ATCC (Manassas, Va.).

Cell culture Many bacterial experiments were performed with *Escherichia coli* and *Bacillus subtilis*. *E. coli* and *B. subtilis* were cultured separately on a Luria-Bertani agar plate, or a nutrition broth agar plate, and kept at 4° C. From the agar plate, *E. coli* or *B. subtilis*, was then collected and seeded into LB at 37° C. or nutrient broth at 30° C. for 8 hours, respectively. The *E. coli* or *B. subtilis* culture was then diluted with its medium to obtain an optical density (OD) at 600 nm of 0.05, and further cultured at 37° C. for 2 hours until an OD of about 1.8 to about 2.5 was obtained. Serial dilution experiments have shown that 1 OD at 600 nm corresponds to about $4 \times 10^8$ cells/mL.

DRCA system and bacterial cell assays The DRCA system was used for these bacterial cell assays. For bacterial cell assays, bacterial cells covered about 90 to about 100% of the bottom surface with the appropriate medium as described above unless stated otherwise. The plates of the cells and compounds were incubated in the instrument for approximately 60 minutes to reach 22° C. All cell assay studies were carried out at about 22° C.

Example 6

Depth Resolved Nuclear Assay (DRNA) To demonstrate the utility of the disclosed SiOG based SPR system for detecting cellular nuclear events occurring at long penetration depths, cell assay platforms have been developed which use chemical or biological pathway modulators, such as fluticasone propionate (FP) (a synthetic corticosteroid derived from fluticasone used to treat, for example, asthma and allergic rhinitis; other trade name products that include fluticasone are Flovent, Flixotide, Flonase, Flixonase, Advair, and Seretide). Fluticasone propionate is a high affinity and selective glucocorticoid receptor (GR) agonist.

Therapeutically, glucocorticoid receptors are of great interest for two reasons. First, mutations in glucocorticoid receptors play a role in Cushing's syndrome (an endocrine disorder caused by excessive levels of cortisol, a corticosteroid), autoimmune diseases, and some cancers. Second, glucocorticoid receptor ligands are already used to treat a variety of medical conditions, such as asthma, rheumatoid arthritis, and leukemia. The use of these ligands in therapy, however, is limited due to negative side effects, such as bone loss, growth retardation, and hypothalamic-pituitary-adrenal axis suppression. A better understanding of the glucocorticoid receptor and its regulation would aid in the search for a glucocorticoid receptor ligand and possibly result in a treatment possessing all of the anti-inflammatory benefits without the disabling side-effects. By measuring the cellular responses triggered by a known pathway modulator using the disclosed SPR system, the ability to detect the nuclear events has been demonstrated. Such a capability has not been available to prior art optical sensor systems, such as the Epic® system (Corning, Inc.) or a conventional SPR platform (e.g., Biacore), due to their limited penetration depth (e.g., less than about 150 to about 200 nm). The disclosed depth resolved cell assay (DRCA) system can offer a broad penetration depth of from about 30 nm to about 1,500 nm. The disclosed DRCA system can provide more information than a platform having a shorter penetration depth.

The disclosure provides methods and a platform to measure and characterize nuclear events of a cell with an optical sensor. As an example, optical sensors including surface plasmon resonance (SPR) sensors can be used to monitor nuclear events of effectors such as pathway modulators. In embodiments, cells can be grown on a treated gold surface. The treatment can be, for example, an organic, inorganic, or biological material that could form a layer for cell attachment, growth, or both. Then the cells were treated with a pathway modulator. The nuclear response was simultaneously monitored using the disclosed multiple wavelength SPR platform, in this case a Corning® Depth Resolved Cell Assay (DRCA) instrument. Depth resolved cell assay results clearly demonstrated nuclear responses.

A specific modulator can be used to trigger the nuclear receptor while multiple optical signals at different penetration depths are detected with DRCA instrument. The nuclear receptor response occurs and can be detected at a deeper penetration depth, for example, the penetration depth should be greater than 200 nm, compared to cell membrane receptor responses.

In embodiments, the at least two different light sources can be, for example, radiation sources operating at different wavelengths, such as from about 300 nm to about 1,700 nm. The SPR signal can be detected by a photodetector, such as an array of photodetectors. Such arrangement provides variable penetration depths of, for example, over about 1,500 nm with a dynamic range several times greater than that of conventional SPR sensor.

As mentioned above, FIG. 2 shows the computed penetration depth versus illumination wavelength for a SiOG based SPR sensor chip of the disclosure (210). The two wavelengths used here were 808 nm and 980 nm. The associated penetration depths are indicated with circles at 356 nm and 572 nm, respectively. For a defined depth such as 572 nm, the DRCA signal output was an integration of signal from the depth range from 0 to 572 nm from the bottom of a cell.

The disclosed DRCA cell assay system uses a sensor chip SPR system to monitor and characterize, in real-time, modulator-induced dynamic cellular events at different penetration depths. Confluent cells are selected to cover the bottom of the gold coated surface of the wells. Then a cell response was modulated with a compound. Modulation of a cellular response can produce values of pharmaceutical interest. For example, fluticasone propionate is a selective high affinity glucocorticoid receptor (GR) agonist used to treat asthma and allergic rhinitis. GlaxoSmithKline currently markets FP as Flovent (US and Canada) and Flixotide (EU) for asthma, and as Flonase (US and Canada) Flixonase (EU and Brazil) for allergic rhinitis, and a combination of fluticasone and salmeterol as Advair (US and Canada) or Seretide (EU). The live whole cell study can be useful to dissect the molecular action mechanism(s) of FP drug. The integrated response signal from a certain depth range was obtained through the cells and recorded by the DRCA optical instrument.

Use of an Optical Sensor for Detection of a Cellular Event
Eukaryotic Cellular Structure A living cell is structurally and functionally analogous to a manufacturing plant. Within a cell, there is cytoplasm, where many proteins and metabolites are distributed. Furthermore many organelles such as nucleus, mitochondria, Golgi, and ribosome, are distributed within a cell, which bodies play a vital role of a cellular function. Different depths across a cell can have unique cellular events going on.

Pathway Modulator

Pathway modulators can have a significant impact on cell biology study and can be a useful tool in drug discovery. Fluticasone propionate (FP) is a synthetic corticosteroid derived from fluticasone used to treat asthma and allergic rhinitis. It is a high affinity and selective glucocorticoid receptor (GR) agonist. GR is a steroid hormone-activated transcription factor involved in the processes of inflammation, glucose homeostasis, bone cell turnover, cell differentiation, and lung maturation. It belongs to the extensive superfamily of nuclear receptors, which includes mineral corticoid, estrogen, progestin, androgen, peroxisome proliferator, vitamin D and thyroid hormone receptors. Molecularly, GR is made up of an N-terminal activation function-1 domain (AF-1), a central DNA binding domain (DBD), and a C-terminal ligand binding domain (LBD). GR ligands are corticosteroid analogs, including dexamethasone and prednisolone. When not bound to a ligand, chaperone proteins such as hsp90 and p23 retain GR in the cytoplasm. Once a hormone binds, the chaperone proteins are released and dimerization occurs, along with nuclear translocation of the entire receptor. Once inside the nucleus, GR can bind to specific DNA promoter elements or 'cross-talk' with specific transcription factors to repress gene activation. The GR is expressed in almost every cell in the human body and regulates genes that control development, metabolism, and immune response. Because the receptor gene is expressed in several forms, it has many different (pleiotropic) effects in different parts of the body. When the GR binds to glucorticoids, its primary mechanism of action is the regulation of gene transcription. A direct mechanism of action involves homodimerization of the receptor, translocation via active transport into the nucleus, and binding to specific DNA responsive elements activating gene transcription. This mechanism of action is referred to as transactivation. The biologic response also depends on the cell type.

Nuclear Receptor Assay

Different penetration or depths of resolution within a cell produced different responses. FIG. 16 shows results of cell assays for nuclear receptors with modulators measured using DRCA methodology, where FP is fluticasone propionate; WV1 is wavelength 808 nm (356 nm depth); WV2 is wavelength 980 nm (572 nm depth); sec is second; where (1610) is WV2-ATP; (1620) is WV1-ATP; (1630) is WV1-FP; (1640) is WV2-FP; (1650) is WV1-buffer; and (1660) is WV2-buffer.

In signal transduction pathways, ATP can be used as a substrate by kinases that phosphorylate proteins and lipids, and by adenylate cyclase, which uses ATP to produce cyclic AMP. ATP binds to P2Y receptors (GPCR) which are present in almost all human tissues where they exert various biological functions based on their G-protein coupling. In addition, ATP is a multifunctional nucleotide in biological energy transformation. The signal curves in FIG. 16 suggests that during the first few minutes, there is a major cellular event near cytoplasm membrane since the short penetration depth had a larger signal than that for the longer penetration depth. One assumption is that ATP binds to P2Y receptors, which in turn triggers a significant cell event(s) shown as a rapid and large change, which could be a conformational change, a mass change near the cytoplasm membrane, or both. If this is the case, it should be possible to see a difference from the different cellular depths. The average response from the wavelength 1 (WV1) should be larger than that from WV2. As time elapsed, the signal dropped significantly. However, since there was no significant difference between the two penetration depths, it may indicate that the cellular event triggered by ATP was more or less evenly distributed among the two depths, if not within the whole cell.

Another significant observation was that the nuclear event triggered by FP at both penetration depths. The results suggest that both 356 nm and 572 nm wavelength and their corresponding penetration depths are within reach of the nucleus of an A431 cell. A retarded response signal, which appeared after 60 minutes, may reflect some late stage cellular process related to a nuclear receptor response. The signal reached plateaus after 6 hours (21,600 seconds). The buffer as a blank did not trigger a significant response.

The specificity of the FP triggered response was also evaluated. Cells were pretreated with the assay buffer or mifepristone for approximately 1 to 2 hours, and the cells were challenged with FP. Mifepristone is a synthetic steroid compound used as a selective antagonist at progesterone (PR) and glucocorticoid (GR) receptors in vitro and in vivo. For GR, it has an higher affinity than dexamethasone. For PR, it is also a silent antagonist and has a higher affinity than progesterone. When the cells were pretreated with antagonist mifepriston (mife), the mifepristone significantly blocked the FP effect on GR, whereas the cells pretreated with the assay buffer did not block FP effect as shown in FIG. 17. FIG. 17 shows the specificity of nuclear receptors measured with DRCA where (1710) is Mife and FP; (1720) is buffer and FP; (1700) is assay buffer alone, and FP is fluticasone propionate; Mife is mifepristone; and sec is second. The results indicated that the major contributor from the FP effect was derived from the glucocorticoid receptor. The assay was specific to the glucocorticoid receptor, one example of a nuclear receptor.

The results demonstrate the method of simultaneous detection of a cellular-nuclear event at different penetration depths with more than one wavelength with the disclosed DRCA system. By changing the penetration depth from, for example, about 50 nm to about 3,000 nm, one can observe a cellular event away for cytoplasm membrane. With multiple combinations of short and long penetration depths, the disclosed DRCA system can differentiate cellular event locations. The disclosed system can provide depth resolved cellular event information from a whole live-cell assay. The disclosed system can provide significant value to, for example, cell biology research and to drug development methodologies.

Regents ATP, Fluticasone propionate, and Mifepristone were purchased from Tocris (St. Louis, Mo.).

Cell culture A431 cells were purchased from American Type Culture Collection (Manassas, Va.). A431 cells were grown in DMEM medium plus 10% fetal bovine serum (FBS) and antibiotics. Cell number of A431 was counted with Beckman-Coulter Particle Counter (Beckman Coulter, Fullerton, Calif.). Approximately $1-2\times10^5$ cells of A431 in 40 microliters medium were seeded in each well of a DRCA 80-well chamber. The wells were coated with a thin-layer of collagen or fibronectin prior to the introduction of the cells. After seeding, the cells were grown in the cell growth incubator at 37° C. for 24 hrs.

DRCA system and cell assays The disclosed DRCA system was used for this experimentation. For cell assays, cell confluence was at from about 90 to about 100% with the appropriate medium as described above unless stated otherwise. The plates of the cells and compounds were incubated in the instrument for approximately 60 minutes to reach 22° C. All studies were carried out at 22° C.

The disclosure has been described with reference to various specific embodiments and techniques. However, it should be understood that many variations and modifications are possible while remaining within the spirit and scope of the disclosure.

What is claimed is:

1. A method for depth resolved sensing of a biological entity, comprising:
    providing a surface plasmon resonance (SPR) sensor system comprising:
        at least one light source providing at least one incident beam, the beam having at least two wavelengths;
        first optics providing incident beam shaping and beam focusing;
        a sensor chip comprising a transparent substrate having on the first face of the substrate a high refractive index prism for receiving the incident focused beam, and having on the second face of the substrate a silicon layer of from about 100 nm to about 5 micrometers, a precious metal layer of from about 30 nm to about 80 nm on the silicon layer;
        second optics providing reflected or emitted beam collection;
        a photodetector for receiving the collected beam and detecting the SPR signal;
        a data acquisition unit; and
        a biological entity on the precious metal outer surface layer of the sensor chip surface;
    irradiating the sensor with the at least two different wavelengths, each of the different wavelengths providing a different penetration depth;
    monitoring each of the different wavelengths for a change in the index of refraction; and
    correlating the change in the index of refraction to a change in the biological entity.

2. The method of claim 1, further comprising contacting the biological entity with a second entity comprising a chemical compound, a second biological entity, or a combination thereof, prior to, during, or after the irradiating the sensor with at least one of the two different wavelengths.

3. The method of claim 1, wherein the biological entity comprises a cell membrane receptor, an intracellular receptor, a cellular nuclear receptor, a subcellular component, or a combination thereof.

4. The method of claim 1, wherein the biological entity comprises a cell, a cell culture, a cell component, a cell construct, a virus, a prion, or a combination thereof.

5. The method of claim 4, wherein the cell culture has a cell density from about 70 to about 100%, the confluence of the cell culture is from about 70 to about 100%, and the assay buffer is Hank's buffered salt solution (HBSS).

6. The method of claim 1, further comprising the precious metal outer surface layer of the sensor chip having an organic polymer, an inorganic polymer, or a combination thereof.

7. The method of claim 1, wherein the biological entity comprises a receptor of a eukaryote cell, a receptor of a prokaryote cell, a synthetic cell construct, a component thereof, or a combination thereof.

8. The method of claim 1, wherein the at least two different wavelengths comprises a plurality of different wavelengths.

9. The method of claim 1, wherein the at least two different wavelengths comprises from three to twenty different wavelengths.

10. The method of claim 2 wherein the second entity is a modulator, an effector, or a combination thereof.

11. The method of claim 1, further comprising a metal interlayer between the silicon and precious metal layers having Cr, Ti, or a combination thereof, and having a thickness of less than 10 nm.

12. The method of claim 1, wherein the at least one light source comprises two different light sources.

* * * * *